US010933173B2

(12) United States Patent
Kaplan et al.

(10) Patent No.: US 10,933,173 B2
(45) Date of Patent: Mar. 2, 2021

(54) SILK FIBROIN-BASED MICRONEEDLES AND METHODS OF MAKING THE SAME

(75) Inventors: David L. Kaplan, Concord, MA (US); Konstantinos Tsioris, Somerville, MA (US); Fiorenzo G. Omenetto, Lexington, MA (US); Eleanor M. Pritchard, New Orleans, LA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 13/880,592

(22) PCT Filed: Oct. 19, 2011

(86) PCT No.: PCT/US2011/056856
§ 371 (c)(1),
(2), (4) Date: Sep. 3, 2013

(87) PCT Pub. No.: WO2012/054582
PCT Pub. Date: Apr. 26, 2012

(65) Prior Publication Data
US 2013/0338632 A1  Dec. 19, 2013

Related U.S. Application Data

(60) Provisional application No. 61/394,479, filed on Oct. 19, 2010.

(51) Int. Cl.
| A61L 31/12 | (2006.01) |
| A61B 17/20 | (2006.01) |
| A61K 9/00 | (2006.01) |
| A61L 31/04 | (2006.01) |
| A61L 31/16 | (2006.01) |
| A61M 5/158 | (2006.01) |
| A61M 37/00 | (2006.01) |

(52) U.S. Cl.
CPC .......... *A61L 31/125* (2013.01); *A61B 17/205* (2013.01); *A61K 9/0021* (2013.01); *A61L 31/047* (2013.01); *A61L 31/16* (2013.01); *A61M 5/158* (2013.01); *A61M 37/0015* (2013.01); *A61M 2037/0046* (2013.01); *A61M 2037/0053* (2013.01)

(58) Field of Classification Search
None
See application file for complete search history.

(56) References Cited

U.S. PATENT DOCUMENTS

| 1,989,005 | A | 1/1935 | Fink et al. |
|---|---|---|---|
| 4,233,212 | A | 11/1980 | Otoi et al. |
| 4,798,722 | A | 1/1989 | Edman et al. |
| 4,820,418 | A | 4/1989 | Hirotsu et al. |
| 5,047,507 | A | 9/1991 | Buchegger et al. |
| 5,290,494 | A | 3/1994 | Coombes et al. |
| 5,606,019 | A | 2/1997 | Cappello |
| 5,728,810 | A | 3/1998 | Lewis et al. |
| 5,770,193 | A | 6/1998 | Vacanti et al. |
| 5,932,462 | A | 8/1999 | Harris et al. |
| 5,994,099 | A | 11/1999 | Lewis et al. |
| 6,106,816 | A | 8/2000 | Hitchen |
| 6,110,590 | A | 8/2000 | Zarkoob et al. |
| 6,123,819 | A | 9/2000 | Peeters |
| 6,175,053 | B1 | 1/2001 | Tsubouchi |
| 6,592,623 | B1 | 7/2003 | Bowlin et al. |
| 6,815,427 | B2 | 11/2004 | Tsubouchi et al. |
| 6,902,932 | B2 | 6/2005 | Altman et al. |
| 7,041,797 | B2 | 5/2006 | Vollrath |
| 7,057,023 | B2 | 6/2006 | Islam et al. |
| 7,285,637 | B2 | 10/2007 | Armato et al. |
| 7,635,755 | B2 | 12/2009 | Kaplan et al. |
| 7,662,409 | B2 | 2/2010 | Masters |
| 7,674,882 | B2 | 3/2010 | Kaplan et al. |
| 7,727,575 | B2 | 6/2010 | Kaplan et al. |
| 7,842,780 | B2 | 11/2010 | Kaplan et al. |
| 7,960,509 | B2 | 6/2011 | Kaplan et al. |
| 8,071,722 | B2 | 12/2011 | Kaplan et al. |
| 2002/0028243 | A1 | 3/2002 | Masters |
| 2002/0138049 | A1* | 9/2002 | Allen .................. A61B 5/1411 604/272 |

(Continued)

FOREIGN PATENT DOCUMENTS

| CA | 2405850 | 10/2002 |
| CA | 2608862 A1 | 12/2005 |

(Continued)

OTHER PUBLICATIONS

Vepari, C., et al. 2007 Prog. Polym. Sci. 32: 991-1007.*
Park et al. 2010 J Korean Phys Soc 56(4): 1223-1277 (NIH Public Access Version) (10 pages) (Year: 2010).*
Agarwal et al., Journal of Applied Polymer Science, 63(3):401-410 (1997). "Effect of Moisture Absorption on the Thermal Properties of Bombyx mori Silk Fibroin Films."
Altman et al., Biomaterials, 23:4131-4141 (2002). "Silk matrix for tissue engineered anterior cruciate ligaments."
Altman et al., Biomaterials, 24:401-416 (2003). "Silk-based biomaterials."

(Continued)

*Primary Examiner* — Marsha Tsay
(74) *Attorney, Agent, or Firm* — Quarles & Brady, LLP

(57) ABSTRACT

A microneedle or microneedle device includes a microneedle body extending from a base to a penetrating tip formed from a silk fibroin based material, which is easy to fabricate and highly biocompatible. The microneedle device can include one or more microneedles mounted to a substrate. The silk fibroin can include active agents to be transported into or across biological barriers such as skin, tissue and cell membranes. The silk fibroin microneedles can be fully or partially biodegradable and/or bioerodible. The silk fibroin is highly stable, affords room temperature storage and is implantable. The silk fibroin structure can be modulated to control the rate of active agent delivery.

24 Claims, 14 Drawing Sheets

(56) References Cited

U.S. PATENT DOCUMENTS

| | | | |
|---|---|---|---|
| 2003/0007991 A1 | 1/2003 | Masters | |
| 2003/0183978 A1 | 10/2003 | Asakura | |
| 2004/0005363 A1 | 1/2004 | Tsukada et al. | |
| 2004/0266992 A1 | 12/2004 | Migliaresi et al. | |
| 2005/0147681 A1 | 7/2005 | Zhao | |
| 2005/0260706 A1 | 11/2005 | Kaplan et al. | |
| 2007/0187862 A1 | 8/2007 | Kaplan et al. | |
| 2007/0212730 A1 | 9/2007 | Vepari et al. | |
| 2008/0058400 A1 | 3/2008 | Yang et al. | |
| 2008/0085272 A1 | 4/2008 | Kaplan et al. | |
| 2008/0293919 A1 | 11/2008 | Kaplan et al. | |
| 2009/0171467 A1 | 7/2009 | Mann et al. | |
| 2009/0182306 A1* | 7/2009 | Lee | A61K 9/0021 604/506 |
| 2009/0202614 A1 | 8/2009 | Kaplan et al. | |
| 2009/0232963 A1 | 9/2009 | Kaplan et al. | |
| 2009/0234026 A1 | 9/2009 | Kaplan et al. | |
| 2009/0297588 A1 | 12/2009 | Rheinnecker et al. | |
| 2010/0028451 A1 | 2/2010 | Kaplan et al. | |
| 2010/0046902 A1 | 2/2010 | Kaplan et al. | |
| 2010/0055438 A1 | 3/2010 | Kaplan et al. | |
| 2010/0063404 A1 | 3/2010 | Kaplan et al. | |
| 2010/0065784 A1 | 3/2010 | Kaplan et al. | |
| 2010/0068740 A1 | 3/2010 | Kaplan et al. | |
| 2010/0070068 A1 | 3/2010 | Kaplan et al. | |
| 2010/0095827 A1 | 4/2010 | Rheinnecker et al. | |
| 2010/0096763 A1 | 4/2010 | Kaplan et al. | |
| 2010/0120116 A1 | 5/2010 | Kaplan et al. | |
| 2010/0178304 A1 | 7/2010 | Wang et al. | |
| 2010/0191328 A1 | 7/2010 | Kaplan et al. | |
| 2010/0196447 A1 | 8/2010 | Kaplan et al. | |
| 2010/0292338 A1 | 11/2010 | Rheinnecker et al. | |
| 2011/0046686 A1 | 2/2011 | Kaplan et al. | |
| 2011/0076384 A1 | 3/2011 | Cannizzaro et al. | |
| 2011/0105402 A1 | 5/2011 | Kim et al. | |
| 2011/0121485 A1 | 5/2011 | Rheinnecker et al. | |
| 2011/0135697 A1 | 6/2011 | Omenetto et al. | |
| 2011/0152214 A1 | 6/2011 | Boison et al. | |
| 2011/0171239 A1 | 7/2011 | Kaplan et al. | |
| 2012/0121820 A1 | 5/2012 | Kaplan et al. | |
| 2012/0123519 A1 | 5/2012 | Lovett et al. | |
| 2012/0231499 A1 | 9/2012 | Lee et al. | |

FOREIGN PATENT DOCUMENTS

| | | |
|---|---|---|
| CN | 1467248 A | 1/2004 |
| CN | 1541724 A | 11/2004 |
| CN | 102917752 A | 2/2013 |
| EP | 0361391 A2 | 4/1990 |
| EP | 1844763 A1 | 10/2007 |
| EP | 1440088 | 5/2008 |
| EP | 2578265 A1 | 4/2013 |
| GB | 1182153 | 2/1970 |
| JP | 55-139427 | 10/1980 |
| JP | 56166235 | 12/1981 |
| JP | 58-38449 | 8/1983 |
| JP | 60-142259 | 7/1985 |
| JP | 60-259677 | 12/1985 |
| JP | 01118544 | 11/1989 |
| JP | 04-263611 | 9/1992 |
| JP | 05163132 | 6/1993 |
| JP | 06-346314 | 12/1994 |
| JP | 08-295697 | 11/1996 |
| JP | 10-36676 | 2/1998 |
| JP | 2000-273264 | 10/2000 |
| JP | 2003192807 | 7/2003 |
| JP | 2004068161 | 3/2004 |
| WO | 1999/001089 | 1/1999 |
| WO | 99/45964 A1 | 9/1999 |
| WO | WO-99/64580 A1 | 12/1999 |
| WO | 2001/036531 | 5/2001 |
| WO | 2001/056626 | 8/2001 |
| WO | 2002/072931 | 9/2002 |
| WO | 2003/022909 | 3/2003 |
| WO | 2003/038033 | 5/2003 |
| WO | 2004/000915 | 12/2003 |
| WO | WO 2004000389 A2 * | 12/2003 ........... A61K 9/0021 |
| WO | 2004/041845 | 5/2004 |
| WO | 2004-062697 A2 | 7/2004 |
| WO | 2005/012606 | 2/2005 |
| WO | 2005-123114 A2 | 12/2005 |
| WO | 2008/052755 A2 | 5/2008 |
| WO | 2008/052775 A2 | 5/2008 |
| WO | 2008/127405 | 10/2008 |
| WO | WO-2009/105564 A2 | 8/2009 |
| WO | 2009/153140 A2 | 12/2009 |
| WO | 2009/156226 | 12/2009 |
| WO | 2010/060600 A1 | 6/2010 |
| WO | 2010-141133 A2 | 12/2010 |
| WO | 2011/006133 | 1/2011 |
| WO | WO-2012/054582 A2 | 4/2012 |

OTHER PUBLICATIONS

Ando et al, Reports on Progress in Polymer Physics in Japan, XXIII:775-778 (1980). "Piezoelectric and Related properties of Hydrated Silk Fibroin."

Asakura et al., Macromolecules, 17:1075-1081 (1984). NMR of silk fibroin 2. 13C NMR study of the chain dynamics and solution structure of Bombyx mori silk fibroin.

Asakura et al., Macromolecules, 18:1841-1845 (1985). "Conformation Characterization of Bombyx Mori Silk Fibroin in the Solid State by High-Frequency 13C Cross Polarization-Magic Angle Spinning NMR, X-ray Diffraction, and Infrared Spectroscopy."

Bini et al., J. Mol. Biol., 335:27-40 (2004). "Mapping Domain Structures in Silks from Insects and Spiders Related to Protein Assembly."

Cai et al., Int. J. Mol. Sci., 11:3529-3539 (2010). "Fabrication of ChitosanlSilk Fibroin Composite Nanofibers for Wound-dressing Applications."

Chao et al., J Biomed Mater Res B Appl Biomater., 95(1):84-90 Author Manuscript (2010). "Silk hydrogel for cartilage tissue engineering."

Chen et al., J Appl Polymer Sci, 65:2257-2262 (1997). "pH sensitivity and ion sensitivity of hydrogels based on complex-forming chitosan/silk fibroin interpenetrating polymer network."

Chen et al., J Appl Polymer Sci, 73:975-980 (1999). "Separation of alcohol-water mixture by pervaporation through a novel natural polymer blend membrane—chitosan/silk fibroin blend membrane—chitosan I silk fibroin blend membrane."

Chen et al., Biomacromolecules, 3:644-648 (2002). "Rheological Characterization of Nephila Spidroin Solution."

Chen et al., J Biomed Mater Res, 67A:559-570 (2003). "Human bone marrow stromal cell and ligament fibroblast responses on RGD-modified silk fibers."

Chen et al., Proteins: Structure, Function, and Bioinformatics, 68:223-231 (2007). "Conformation transition kinetics of Bombyx mori silk protein."

Chen et al., Food Research International, 44:1468-1475 (2011). "Improvement of physicochemical stabilities of emulsions containing oil droplets coated by non-globular protein-beet pectin complex membranes."

Demura et al., Biosensors, 4:361-372 (1989). "Immobilization of biocatalysts with Bombyx mori silk fibroin by several kinds of physical treatment and its application to glucose sensors."

Demura et al., J Membrane Science, 59:39-52 (1991). "Porous membrane of Bombyx mori silk fibroin: structure characterization, physical properties and application to glucose oxidase immobilization."

Derwent Record, Abstract of JP 08295697 A2 "Production of aqueous solution of silk fibroin at high concentration." Nov. 12, 1996.

Doshi et al. J Electrostatics, 35:151-160 (1995). "Electrospinning process and applications of electrospun fibers."

Dyakonov et al., Journal of Drug Delivery, Article 490514 (2012). "Design and Characterization of a Silk-Fibroin-Based Drug Delivery Platform Using Naproxen as a Model Drug."

(56) References Cited

OTHER PUBLICATIONS

Freddi et al., J Appl Polymer Sci, 56:1537-1545 (1995). "Silk fibroin/cellulose blend films: preparation, structure, and physical properties."
Furst et al., Ann Thorac Surg, 79:1522-1529 (2005). "Release of Glutaraldehyde From an Albumin-Glutaraldehyde Tissue Adhesive Causes Significant In Vitro and In Vivo Toxicity."
Gill et al., Urology, 65:463-466 (2005). "Improved Hemostasis During Laparoscopic Partial Nephrectomy Using Gelatin Matrix Thrombin Sealant."
Hijirida et al., Biophysical Journal, 71:3442-3447 (1996). "13C NMR of Nephila clavipes major ampullate silk gland."
Hinman et al., TIBTECH, 18:374-379 (2000). "Synthetic spider silk: a modular fiber."
Hofmann et al., Journal of Controlled Release, 111:219-227 (2006). "Silk fibroin as an organic polymer for controlled drug delivery."
Horan et al., Biomaterials, 26:3385-3393 (2005). "In vitro degradation of silk fibroin."
Hu et al., Biomacromolecules, 12:1686-1696 (2011). "Regulation of Silk Material Structure by Temperature-Controlled Water Vapor Annealing."
Huang et al., J Biomater Sci Polymer Edn, 12(9):979-993 (2001). "Engineered collagen—PEO nanofibers and fabrics."
Huang et al., Macromolecules, 33:2989-2997 (2000). "Generation of synthetic elastin-mimetic small diameter fibers and fiber networks."
Jang et al., Oral Surg Oral Med Oral Pathol Oral Radiol Endod, 109:831-836 (2010). "Restoration of peri-implant defects in immediate implant installations by Choukroun platelet-rich fibrin and silk fibroin powder combination graft."
Jenkins et al., Surgery, 20:124-132 (1946). "Clinical and Experimental Observations on the Use of Gelatin Sponge or Foam."
Jiang et al., Materials Letters, 60:919-925 (2006). "Tensile behavior and morphology of differently degummed silkworm (Bombyx mori) cocoon silk fibres."
Jin et al., Biomacromolecules, 3:1233-1239 (2002). "Electrospinning Bombyx mori silk with poly(ethylene oxide)."
Jin et al., Adv. Funct. Mater., 15:1241-1247 (2005). "Water-Stable Silk Films with Reduced β-Sheet Content."
Jin et al., Nature, 424:1057-1061 (2003). "Mechanism of silk processing in insects and spiders."
Kim et al., Biomacromolecules, 5:786-792 (2004). "Structure and Properties of Silk Hydrogels."
Kweon et al., J Appl Polymer Sci, 80:1848-1853 (2001). "Preparation of semi-interpenetrating polymer networks composed of silk fibroin and poly(ethylene glycol) macromer."
Lawrence et al., Biomaterials, 30(7):1299-1308 Author Manuscript (2009). "Silk film biomaterials for cornea tissue engineering."
Lazaris, Science, 295:472-476 (2002). "Spider silk fibers spun from soluble recombinant silk produced in mammalian cells."
Lee et al., Oral Surg Oral Med Oral Pathol Oral Radiol Endod, 109:e33-e38 (2010). "A combination graft of low-molecular-weight silk fibroin with Choukroun platelet-rich fibrin for rabbit calvarial defect."
Leisk et al., Adv. Mater., 22:711-715 (2010). "Electrogelation for Protein Adhesives."
Li et al., Biomaterials, 27:3115-3124 (2006). "Electrospun Silk-BMP-2 scaffolds for bone tissue engineering."
Li et al., J Mater Sci: Mater Med, 19:577-582 (2008). "Effect of silicon on the formation of silk fibroin/calcium phosphate composite."
Liang et al., J Appl Polymer Sci, 45:1937-1943 (1992). "Improvements of the physical properties of fibroin membranes with sodium alginate."
Lin et al., Pharmaceutical Research, 26(3):631-643 (2008). "PEG Hydrogels for the Controlled Release of Biomolecules in Regenerative Medicine."
Lowe et al., J Cardiovasc Surg, 48(3):323-331 (2007). "Evaluation of the topical hemostatic efficacy and safety of TISSEEL VH S/D fibrin sealant compared with currently licensed TISSEEL VH in patients undergoing cardiac surgery: A phase 3, randomized double-blind clinical study."
Lu et al., Biomacromolecules, 10:1032-1042 (2009). "Stabilization of Enzymes in Silk Films."
Lu et al., Acta Biomater. 6(4):1380-1387 (2010). "Water-Insoluble Silk Films with Silk I Structure."
Marcovich et al., Urology, 57:806-810 (2001). "Comparison of 2-Octyl Cyanoacrylate Adhesive, Fibrin Glue, and Suturing for Wound Closure in the Porcine Urinary Tract."
Megeed et al., Pharmaceutical Research, 19(7):954-959 (2002). "Controlled release of plasmid DNA from a genetically engineered silk-elastinlike hydrogel."
Nazarov et al., Biomacromolecules, 5:718-726 (2004). "Porous 3-D Scaffolds from Regenerated Silk Fibroin."
Pandit et al., Archives of Biochemistry and Biophysics, 149:259-268 (1972). "Studies on Silk Fibroin. I. Molecular Weight, Sedimentation Coefficient, Viscosity and Optical Rotation of Silk Fibroin from Carbonate-Extracted Silk Fiber."
Petrini et al., Journal of Materials Science: Materials in Medicine, 12:849-853 (2001). "Silk fibroin-polyurethane scaffolds for tissue engineering."
Preul et al., J Neurosurg, 107:642-650 (2007). "Application of a hydrogel sealant improves watertight closures of duraplasty onlay grafts in a canine craniotomy model."
Pritchard et al., Macromol. Biosci., 13:311-320 (2013). "Effect of Silk Protein Processing on Drug Delivery from Silk Films."
Rajkhowa et al., Journal of Applied Polymer Science, 119:1339-1347 (2011). "Molecular Weight and Secondary Structure Change in Eri Silk During Alkali Degumming and Powdering."
Reneker et al., Nanotechnology, 7:216-223 (1996). "Nanometre diameter fibres of polymer, produced by electrospinning."
Samal et al., Macromol. Mater. Eng., DOI: 10.1002/mame.201200377 (2013). "Ultrasound Sonication Effects on Silk Fibroin Protein."
Sawyer et al., JAMA, 191(9):740-742 (1965). "Dextran therapy in thrombophlebitis." Abstract.
Silva et al., Macromol. Biosci., 8:000-000 (2008). "Genipin-Modified Silk Fibroin Nanometric Nets."
Soffer et al., J Biomater Sci Polym Ed., 19(5):653-664 Author Manuscript (2008). "Silk-Based Electrospun Tubular Scaffolds for Tissue Engineered Vascular Grafts."
Sofia et al., Journal of Biomedical Materials Research, 54(1):139-148 (2001). "Functionalized silk-based biomaterials for bone formation."
Spotnitz et al., Transfusion, 48:1502-1516 (2008). "Hemostats, sealants, and adhesives: components of the surgical toolbox."
Torchiana, J Card Surg, 18:504-506 (2003). "Polyethylene Glycol Based Synthetic Sealants: Potential Uses in Cardiac Surgery."
Tsukada et al., J. of Applied Polymer Science, 54(4):507-514 (1994). "Preparation and Application of Porous Silk Fibroin Materials."
U.S. Appl. No. 60/906,509, filed Mar. 13, 2007 by Omenetto et al.
U.S. Appl. No. 61/224,618, filed Jul. 10, 2009 by Numata et al.
Vanderhooft et al., Biomacromolecules, 8:2883-2889 (2007). "Synthesis and Characterization of Novel Thiol-Reactive Poly(ethylene glycol) Cross-Linkers for Extracellular-Matrix-Mimetic Biomaterials."
Wallace et al., J Biomed Mater Res (Appl Biomater), 58:545-555 (2001). "A Tissue Sealant Based on Reactive Multifunctional Polyethylene Glycol."
Wang et al., Langmuir, 21:11335-11341 (2005). "Biomaterial coatings by stepwise deposition of silk fibroin."
Wang et al., J Control Release, 134(2):81-90 (2009). "Growth Factor Gradients via Microsphere Delivery in Biopolymer Scaffolds for Osteochondral Tissue Engineering."
Wenk, Diss. Eth No. 18659 (2009). "Silk Fibroin as a Vehicle for Drug Delivery in Tissue Regeneration."
Wheat et al., Urol Clin North Am., 36(2):265-275 (2009). "Advances in Bioadhesives, Tissue Sealants, and Hemostatic Agents."
Wilson et al., PNAS, 98(24):13660-13664 (2001). "Surface organization and nanopatterning of collagen by dip-pen nanolithography."

(56) References Cited

OTHER PUBLICATIONS

Wray et al., J Biomed Mater Res Part B, 99B:89-101 (2011). "Effect of Processing on silk based biomaterials: Reproducibility and biocompatibility."

Yamada et al., Materials Science and Engineering C, 14:41-46 (2001). "Preparation of undegraded native molecular fibroin solution from silkworm cocoons."

Yamada et al., Thin Solid Films, 440:208-216 (2003). "AFM observation of silk fibroin on mica substrates: morphologies reflecting the secondary structures."

Yucel et al., J. Struct Biol., 170(2):406-412 (2010). "Non-equilibrium Silk Fibroin Adhesives."

Zhou et al., Proteins: Structure, Function, and Genetics, 44:119-122 (2001). "Silk Fibroin: Structural Implications of a Remarkable Amino Acid Sequence."

Zhou et al., Chem Commun, 2518-2519 (2001). "Preparation of a novel core-shell nanostructured gold colloid-silk fibroin bioconjugate by the protein in situ redox technique at room temperature."

Extended European Search Report for EP 11835053.7, 15 pages (dated Jul. 23, 2014).

International Search Report for PCT/US2011/056856, 5 pages (dated May 21, 2012).

Written Opinion for PCT/US2011/056856, 6 pages (dated May 21, 2012).

You, X. et al., Rapidly dissolving fibroin microneedles for transdermal drug delivery, Materials Science and Engineering C, 31(8):1632-1636 (2011).

European Patent Office, Extended European Search Report for application 18193586.7, dated Mar. 27, 2019, 11 pages.

Sullivan, S. P., et al. "Minimally invasive protein delivery with rapidly dissolving polymer microneedles." Advanced materials 20.5 (2008): 933-938.

You, X et al. "Rapidly dissolving silk protein microneedles for transdermal drug delivery." 2010 IEEE International Conference on Nano/Molecular Medicine and Engineering. IEEE, 2010.

* cited by examiner

Micro patterned photoresist

Anisotropic SF$_6$ RIE patterned Si$_3$N$_4$

Isotropic HNA wet etched Si

Released Si microneedle molds

Drug loaded silk microneedle structures

Al Master

PDMS mold

Al Master

702

PDMS mold

700

Drug loaded silk solution

PDMS mold

Dried silk structures

PDMS mold

Drug loaded silk microneedles

Enzyme Activity
HRP release in collagen

SILK FIBROIN-BASED MICRONEEDLES AND METHODS OF MAKING THE SAME

CROSS REFERENCE TO RELATED APPLICATIONS

This application is a 35 U.S.C. § 371 National Phase Entry Application of International Application No. PCT/US2011/056856 filed Oct. 19, 2011, which designates the U.S., and which claims the benefit under 35 U.S.C. § 119(e) of U.S. Provisional Application No. 61/394,479, filed Oct. 19, 2010, the content of which is incorporated herein by reference in its entirety.

GOVERNMENT SUPPORT

This invention was made with government support under grant EB002520 awarded by the National Institutes of Health. The government has certain rights in the invention.

FIELD OF INVENTION

The present invention generally relates to microneedles and microneedle devices, and methods of making and using the same.

BACKGROUND OF THE INVENTION

Transdermal administration can represent a useful route for drug and vaccine delivery due to the ease of access and avoidance of macromolecular degradation in the gastrointestinal tract [1]. Microneedles have become a safe and relatively pain-free alternative to hypodermic needles for transdermal drug delivery. Traditional materials used in the fabrication of microneedles, metals and synthetic polymers, are associated with various restrictions, however, that compromise their production and performance.

One current microneedle technology utilizes a dissolvable poly-lactide-co-glycolide (PLGA) polymer microneedle body loaded with microparticles (either PLGA or carboxymethylcellulose) filled with the drug of interest to provide sustained drug release [2]. However, the fabrication method for this microneedle system constitutes a limitation, as polymer melting temperatures above 135° C. and vacuum are necessary for processing and these conditions can be detrimental to various temperature-sensitive drugs, particularly peptides and proteins.

Recently-developed microneedle systems employ room temperature processing by coating solid metallic microneedle structures with polymer (a blend of carboxymethylcellulose, Lutrol F-68NF and D-(+)-trehalose dehydrate) containing an influenza vaccine [3]. While the activity of the incorporated vaccine can be partially preserved during processing [4, 5], the coating approach to microneedle drug loading provides only a small volume to entrap therapeutic substances compared to bulk loaded structures. Further metal-based microneedle systems have limitations that compromise their function, such as the risk of breaking if improperly applied [6] and the possibility of an inflammatory response or infection if small metal structures remain in the skin.

Bulk-loaded microneedles have been fabricated from biocompatible and dissolvable materials such as polyvinylpyrrolidone (PVP) and carbohydrates [3, 7]. Relatively large doses can be administered due to the bulk loading of this dissolvable system. The polymers can be cured at room temperature. However, while drug degradation caused by elevated temperatures during processing can be avoided, curing by ultraviolet light can impact the activity of the incorporated drug. In addition, there is a limited control over drug release kinetics using these polymeric microneedle systems. Due to rapid dissolution of the polymeric microneedles, relatively short term burst delivery has been achieved so far. Thus, there remains a strong need for biocompatible, robust and effective drug-delivery microneedles, and improved approaches to the manufacture of such microneedles.

SUMMARY OF THE INVENTION

Microneedles can be efficient, easily applied, and relatively painless, but currently pose various limitations such as inabilities to precisely control the release kinetics of drugs, limited drug-loading capacity, reduced or inactivated drug activity during processing conditions, and the onset of local infections at the needle-skin interface. To this end, the inventors have developed a biocompatible silk fibroin-based microneedle that is mechanically robust, stabilizes the activity of active agents in the microneedle, and allows programmable degradability of the microneedle for controlled drug release behavior. Further, since active agents such as antibiotics can be stabilized in the silk fibroin-based microneedles, control of infections at the site of injection can be also beneficial.

Accordingly, aspects of the present invention provide for silk fibroin-based microneedles and microneedle devices for transport or delivery of active agents, including drugs and biological molecules, across biological barriers, such as skin, tissue or cell membranes; and methods of making and using the same. In one aspect, provided herein is a microneedle comprising silk fibroin, wherein the microneedle includes a microneedle body extending from a base to a penetrating tip, for example, by a predefined distance. The penetrating tip can have a diameter of any size, based upon types of biological barriers, and/or users' needs or applications. In some embodiments, the penetrating tip can have a dimension (e.g., diameter) ranging from about 50 nm to about 50 µm, e.g., including from about 200 nm to about 40 µm or from about 300 nm to about 30 µm. In some embodiments, the penetrating tip can have a dimension (e.g., diameter) ranging from less than 500 nm to about 2 µm. In some embodiments, the penetrating tip can have a dimension (e.g., diameter) ranging from about 300 nm to about 30 µm. In some embodiments, the penetrating tip can have a dimension (e.g., diameter) of greater than 50 µm or smaller than 50 nm. The length of the microneedle body can be selected to position the penetrating tip at a predefined distance from the base to provide tissue penetration of a predefined depth for delivery of an active agent. In some embodiments, the silk fibroin microneedle can have a body length of about 15 µm to about 1500 µm or from about 200 µm to about 800 µm.

In various embodiments, the silk fibroin-based microneedle can further comprise at least one additional material, wherein the additional material can be dispersed throughout the microneedle or forms a portion of the microneedle. The additional material can be a pore-forming agent, a structural component, biosensor, or an active agent for release, optionally with an additional excipient or adjuvant.

In certain embodiments, the silk fibroin-based microneedle can further comprise an active agent, e.g., vaccine, antibiotics, hormones, peptides, antibodies and antibody-like fragments. In such embodiments, the active agent can retain at least about 30% of its original bioactivity when the microneedle is maintained for at least about 24 hours or longer at a temperature above 0° C., e.g., at about room temperature, upon storage or transportation. Accordingly, a microneedle for storing and delivering at least one active agent is also provided herein. Such microneedle comprises at least one active agent and silk fibroin, wherein said microneedle has a base and a penetrating tip with a tip diameter ranging from about 50 nm to about 40 μm, and wherein the active agent retains at least about 30% of its original bioactivity when the microneedle is maintained for at least about 24 hours at a temperature above 0° C. In some embodiments, the active agent is an immunogen, e.g., a vaccine.

In certain embodiments, at least about 10% or more of the active agent dispersed in the microneedles can be released into a biological barrier upon administration over a period of at least about 24 hours or longer.

Another aspect provided herein is a microneedle device comprising a substrate and one or more silk fibroin microneedles described herein, wherein the silk fibroin microneedles are integrated or attached to the substrate and extend from the substrate; and each silk fibroin microneedle comprises a base and a penetrating tip. The base of the microneedle can be mounted to the substrate or formed as part of the substrate that can be rigid or flexible, for example, in the form of a film to conform to the surface of the treatment site. In some embodiments, a microneedle device of the present invention can include a substrate and one or more silk fibroin microneedles projecting from the substrate, preferably by a predefined distance.

In some embodiments, each microneedle can extend from the substrate to the same distance or to a different distance, thus a predefined profile of constant or varying microneedle depth penetrations can be provided in a single device. The length of each microneedle body can be selected to position the penetrating tip at a predefined distance from the base to provide tissue penetration to a predefined depth for delivery of at least one active agent.

A plurality of microneedles can be arranged in a random or predefined pattern, such as an array. The distance between the microneedles and the arrangement of the plurality of microneedles can be selected according to the desired mode of treatment and characteristics of the treatment site. The microneedles can be biodegradable, bioerodible or otherwise designed to leave at least a portion of the microneedle in the tissue penetrated. Typically, the base and body of the microneedle will have the same diameter or larger than the tip. The shape and diameter of the microneedle body can be selected according to the desired mode of treatment and the characteristics of the treatment site.

Methods for fabricating the silk fibroin-based microneedles and silk fibroin-based microneedle devices are also provided herein. In some embodiments, such fabrication methods involve mild processing conditions, thus maintaining bioactivity of active agents dispersed in the microneedles described herein.

A further aspect of the invention relates to methods for delivering at least one active agent to cross or get into a biological barrier. The method includes providing a microneedle comprising silk fibroin and the active agent; causing the microneedle to penetrate into the biological barrier, and allowing the active agent to be released from the microneedle.

In some embodiments of any aspects described herein, the silk fibroin used for fabrication of the microneedles can be regenerated silk fibroin. In some embodiments, silk fibroin can be sericin-depleted.

BRIEF DESCRIPTION OF THE DRAWINGS

FIGS. 3A-3K show exemplary steps of a schematic process for fabricating one or more embodiments of the invention comprising silk fibroin microneedles. FIG. 3A shows silicone (Si) wafer with a 200 nm thick low stress silicone nitride ($Si_3N_4$) layer as a substrate for fabrication of a microneedle molding master. FIG. 3B shows that the wafer is coated with 1 μm positive tone photoresist (S1813, Rohm & Haas). FIG. 3C shows that photolithography is performed, leaving circular photoresist patterns functioning as a mask for the subsequent etching step. FIG. 3D shows that anisotropic reactive ion etching (RIE) is performed with $SF_6$ gas to etch the patterned $Si_3N_4$ film and expose the underlying Si material. FIG. 3E shows a timed isotropic wet etch performed with a mixture of hydrofluoric-, nitric- and acetic acid (HNA) to undercut the Si3N4 mask. FIG. 3F shows that a brief ultrasonic bath removes the residual $Si_3N_4$ circular mask and exposes the underlying Si microneedle molds. FIG. 3G shows polydimethylsiloxane (PDMS) polymer being poured over the positive Si microneedle molds and cured. FIG. 3H shows the negative PDMS mold after removed from the Si master. FIG. 3I shows blending aqueous silk fibroin solution with the desired drug. FIG. 3J shows drug-loaded silk fibroin solution being poured over the PDMS mold and the solution being allowed to dry to form a drug-loaded silk fibroin film. FIG. 3K shows one embodiment of the drug-loaded silk fibroin-based microneedle device after removed from the PDMS mold.

FIG. 4A shows one embodiment of a Si microneedle molding master, bottom diameter 150 μm, height 60 μm and tip radius <500 nm. FIG. 4B shows a silk microneedle structure replicating the original Si master, e.g., the one shown in FIG. 4A, with high accuracy. FIG. 4C shows a magnified view of the silk microneedle tip of FIG. 4B, measuring <2 μm in diameter.

FIG. 6A shows a series of photographs of hydrated silk fibroin films loaded with reactive red-120 dye (a model dye, MW=~1500). FIG. 6B shows cumulative release behavior of the various methanol-treated (at several concentrations for different treatment durations) silk fibroin films loaded with reactive red-120 dye. FIG. 6C shows the effect of methanol treatment (at indicated concentrations for the two different treatment times) on film permeability of the silk fibroin films loaded with a reactive red-120 dye.

FIG. 7A shows an aluminum (Al) master manufactured by high speed milling and chemical wet etching. FIG. 7B shows PDMS casted over the Al master to produce a negative PDMS mold. FIG. 7C shows the negative PDMS mold removed from the Al master. FIG. 7D shows that drug-loaded silk fibroin solution is casted over the PDMS mold. FIG. 7E shows that drug-loaded silk fibroin solution is allowed to dry to form drug-loaded silk fibroin microneedles. FIG. 7F shows one or more embodiments of the drug-loaded silk microneedles described herein (after removed from the PDMS mold).

FIG. 8A shows an example of an Al needle template after mechanical milling. FIG. 8B shows an example of an Al microneedle master after 20 minutes of chemical etching. FIG. 8C shows a macroscopic view of an exemplary Al microneedle master. FIG. 8D shows an example of an Al microneedle master after 2 hours of chemical etching. FIG. 8E shows a macroscopic view of an exemplary silk microneedle patch, which is incorporated with reactive red-120 dye, in one embodiment, e.g., for the purpose of visualization. FIG. 8F shows one or more embodiments of silk fibroin microneedles. The silk fibroin microneedles were loaded with reactive red-120 dye for the purpose of visualization.

FIG. 9A shows a schematic scheme depicting an exemplary experimental setup to assess drug-loaded silk fibroin microneedles in an in vitro hydrogel skin model. Silk fibroin microneedles penetrate a polymer membrane and a collagen hydrogel to subsequently release a model drug in a controlled fashion. FIG. 9B shows that bioactivity of microneedle-released horseradish peroxidase enzyme (HRP) into the collagen slab after 5 minutes and 2 hrs releases was detected by chromogenic substrate. FIG. 9C shows the total model drug release of silk fibroin microneedles in collagen hydrogels, as determined from collagenase digestion and absorption spectroscopy, over a period of time, e.g., over 40 hours. The insert of FIG. 8C depicts the early events of model drug release from silk fibroin microneedles into the collagen hydrogels (N=3, error bars represent standard deviations).

FIG. 10A shows representative photographs of the zones of clearance in *S. aureus* lawns exposed to tetracycline-loaded silk fibroin microneedles and control silk fibroin microneedles. FIG. 10B shows average colony forming unit (CFU) counts for *S. aureus* lawns exposed to tetracycline-loaded silk fibroin microneedles and control silk microneedles in $10^6$ CFU per 10-mm diameter agar biopsy sample. N=3, error bars represent standard deviations.

DETAILED DESCRIPTION OF THE INVENTION

Figure 1:
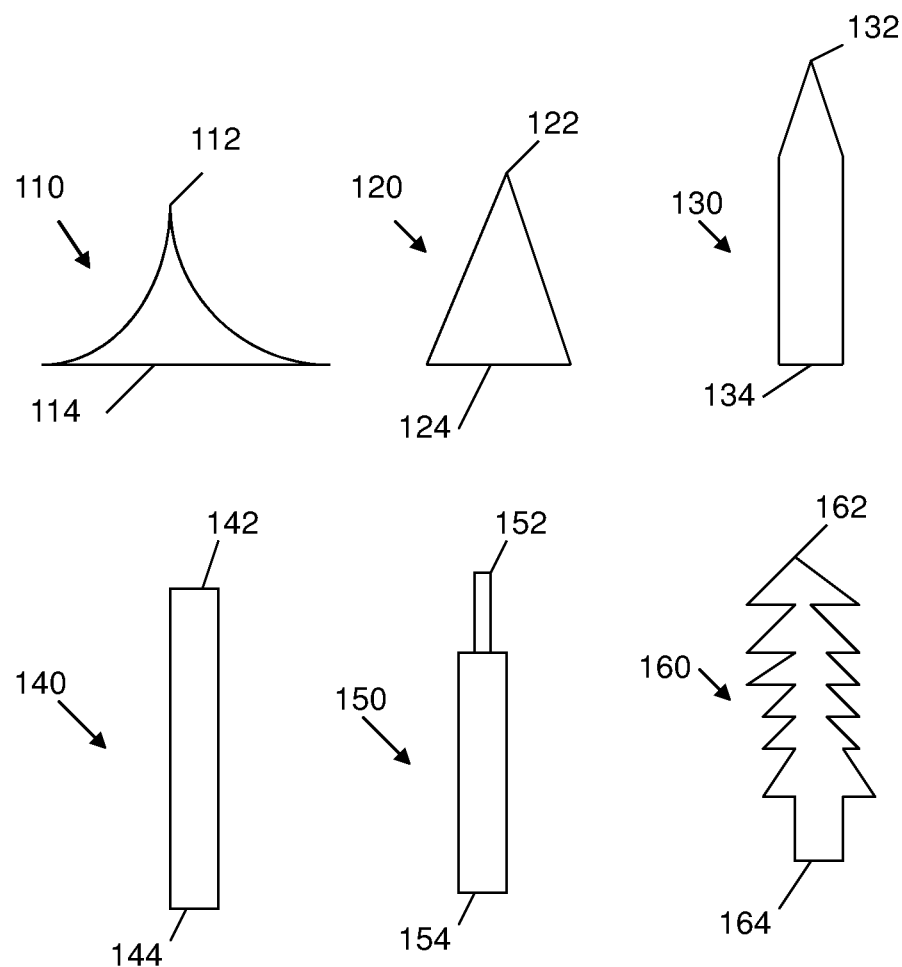
FIG. 1 is a diagrammatic view of exemplary microneedles, according to one or more embodiments of the invention.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Traditional materials used in the fabrication of microneedles, metals and synthetic polymers, are associated with various restrictions, therefore compromising their performance. Ideally, microneedle systems require fabrication from mechanically robust, biocompatible materials, and/or biodegradable materials that dissolve in the patient's body if implanted. Davis et al., 37 J. Biomech. 1155 (2004); Sullivan et al., 20 Adv. Mats. 933 (2008). Silk fibroin has proven to be an excellent biopolymer material for biomedical applications due to a variety of material properties including excellent mechanical properties, biocompatibility, and biodegradability. Altman et al., 24 Biomats. 401 (2003); Jiang et al., 17 Adv. Functional Mats. 2229 (2007).

Active agents including, but not limited to, proteins, antibiotics, enzymes, drugs, nucleic acids (e.g., DNA, RNA), vaccines, antibodies and antibody-like fragments, can be incorporated into the silk fibroin matrix due to the all-aqueous processing. Silk fibroin provides a biologically favorable microenvironment that allows the inclusion of various biological and/or chemical dopants and maintains their functionality. Proteins (Bini et al., 335 J. Mol. Bio. 27 (2004)), enzymes (Lu et al., Stabilization of Enzymes in Silk Films, 10 Macromol. Biosci. 359 (2009)), and small organics (Lawrence et al., 9 Biomacromol. 1214 (2008)), have been incorporated into silk matrices for various biochemical functionalities. Additionally, these agents can be released in a controlled fashion from these silk materials. Moreover, bioactive species can be preserved in a dry form for extended periods of time without concern for the cold-chain. Lu et al., Biomacromol. 217 (2009). Due to these potential properties, silk was investigated as a useful material for the fabrication of transdermal microneedles and microneedle devices for drug delivery. In this regard, the stability that silk fibroin provides to bioactive agents can be harnessed to provide, in the microneedle device itself, both stable storage and efficacious delivery of a variety of important agents, such as vaccines, insulin, and emergency drugs.

For successful transdermal drug delivery, microneedles must transfer the active agent across the outside layer of the skin (stratum corneum), while minimizing or avoiding pain. Glass, metal and PLGA copolymer microneedle lengths between 15 μm to 500 μm are effective for drug delivery and cause little or no pain. Henry et al., 87 J. Pharm. Sci. 922 (1998); Arora et al., 364 Intl. J. Pharm. 227 (2008). Various microneedle designs have been described. Reed & Lye, 92 IEEE 56 (2005). Typically, these microneedles are either hollow or surface-coated with the agent to be administered. McAllister et al., 100 PNAS 13755 (2003). More recently, dissolving microneedles fabricated from carboxymethylcellulose (600 μm height, 300 μm base, and 600 μm center-to-center spacing) or amylopectin were used to encapsulate and deliver proteins across cadaver pig skin. Centrifugation of the needle mold was required, however, to overcome critical buckling load issues in these microneedles. Lee et al., Dissolving Microneedles for Transdermal Drug Delivery, 29 Biomats. 2113 (2008). The embodiments of the present invention provide a simple but elegant design approach based on silk fibroin, in which agent can be loaded within or on the microneedle matrix, that allows easy adjustment of microneedle size, active agent load, and release profiles to accommodate different applications. In some embodiments, the silk fibroin microneedles of the present invention are sharper and stiffer than those of other polymers. In some embodiments, the active agents distributed in the microneedles described herein can be stabilized over an extended period of time. In some embodiments, the release of active agents from the microneedles and/or microneedle devices described herein can be controlled, e.g., by modulating the amount of beta-sheet structure within the silk fibroin matrix.

Microneedles

One aspect provided herein relates to microneedles comprising silk fibroin. Such microneedles each have a base and a penetrating tip, wherein the penetrating tip has a dimension ranging from about 50 nm to about 50 μm. By way of example only, exemplary embodiments of microneedles 110, 120, 130, 140, 150, 160 according to the present invention are shown in FIG. 1, wherein each microneedle includes a silk fibroin microneedle body 110, 120, 130, 140, 150, 160 extending from a base 114, 124, 134, 144, 154, 164 to a penetrating tip 112, 122, 132, 142, 152, 162.

As used therein, the term "penetrating tip" refers to an end of a microneedle that is adapted to first contact and penetrate a surface, e.g., of a biological barrier. The penetrating tip can be of any shape and/or dimension. The penetrating tip can have a shape of various geometries, e.g., but not limited to, circles, rectangles, squares, triangles, polygons, and irregular shapes. In some embodiments, the penetrating tip can appear as a point, for example, due to limited resolution of optical instruments, e.g., microscopes, and/or of human eyes. In some embodiments, the shape of the penetrating tip can be the same as or different from that of the cross section of the microneedle body.

The term "dimension" as used herein generally refers to a measurement of size in the plane of an object. With respect to a penetrating tip of the microneedles described herein, in some embodiments, the dimension of a penetrating tip can be indicated by the widest measurement of the shape of the penetrating tip. For example, the dimension of a circular tip can be indicated by the diameter of the circular tip. In accordance with the invention, the penetrating tip can have a dimension (e.g., a diameter) ranging from about 50 nm to about 50 μm, including from about 100 nm to about 40 μm, from about 200 nm to about 40 μm, from about 300 nm to about 30 μm, from about 500 nm to about 10 μm, or from about 1 μm to about 10 μm. In some embodiments, the penetrating tip can have a dimension (e.g., a diameter) ranging from about 50 nm to about 10 μm, e.g., from about 50 nm to about 8 μm, from about 100 nm to about 5 μm, or from about 100 nm to about 2 μm. In other embodiments, the penetrating tip can have a dimension (e.g., a diameter) of less than 50 nm, or greater than 50 μm. Compared to previous polymer-based dissolvable microneedle designs (generally with a penetrating tip having a dimension of more than 10 μm [9]), some embodiments of the microneedles described herein can have sharper tips (e.g., less than 10 μm, 5 μm or 2 μm), thus increasing the probability of each microneedle penetrating a tissue (e.g., skin) and in turn increasing the overall amount of an active agent administered into the tissue.

The base of the microneedles described herein is generally the opposite end of the penetrating tip. The base of the microneedles can be attached or secured to a solid substrate or a device for facilitating the penetration of the microneedles into a biological barrier. The base of the microneedle can be of any size and/or shape. The base can have a shape of various geometries, e.g., but not limited to, circles, rectangles, squares, triangles, polygons, and irregular shapes. In various embodiments, the shape of the base can follow that of the cross section of the microneedle body.

Generally, the base of the microneedles described herein is the widest portion of the microneedles, e.g., the base 114, and 124 are the widest part of the microneedles 110 and 120. However, in some embodiments, the base and the body of the microneedles can have substantially the same width, e.g., the base 134, 144 and the body 130, 140 of the microneedles 130, 140 have substantially the same width. In some embodiments, the base, the body and the penetrating tip of the microneedle can have substantially the same width, as shown in the microneedle 140 having a uniform width along the entire microneedle body from the base 144 to the penetrating tip 142. A skilled artisan can determine an appropriate base dimension based on a number of factors, including, but not limited to, the length and aspect ratio of the microneedle body, the type of surfaces to be penetrated, and mechanical property of silk fibroin. In some embodiments, the base dimension (e.g., a diameter) of the microneedles can range from 50 nm to about 1500 μm, from about 50 nm to about 1000 μm, from about 100 nm to about 750 μm, from about 250 nm to about 500 μm, or from about 500 nm to about 500 μm.

The microneedles described herein can be in any elongated shape suitable for use in tissue piercing, with minimal pain to a subject. For example, without limitations, the microneedle can be substantially cylindrical, wedge-shaped, cone-shaped, pyramid-shaped, irregular-shaped or any combinations thereof.

The shape and/or area of the cross section of the microneedles described herein can be uniform and/or vary along the length of the microneedle body. The cross-sectional shape of the microneedles can take a variety of shapes, including, but not limited to, rectangular, square, oval, circular, diamond, triangular, elliptical, polygonal, U-shaped, or star-shaped. In some embodiments, the cross section of the microneedles can have a uniform shape and area along the length of the microneedle body, e.g., as illustrated by the microneedle 140 with a straight body of uniform cross sections (having a uniform shape and area) along its body length. In some embodiments, the cross section of the microneedles can have the same shape, with a varying area along the length of the microneedle body. For example, as shown in FIG. 1, the microneedle 110, 120, or 150 can comprise a tapered body with decreasing crosssectionals areas of the same shape toward the penetrating tip 112, 122, or 152; or the microneedle 160 can have varying cross-sectional areas of the same shape along the length of the microneedle body. In some embodiments where the microneedles are irregular-shaped, their cross sections can vary in both shape and area along the length of the microneedle body, or their cross sections can vary in shape (with a constant area) along the length of the microneedle body. In one embodiment, the microneedles described herein comprise a tapered body with a substantially circular cross section along the length of the microneedle body. The cross-sectional dimensions of the microneedle body can range from 50 nm to about 1500 µm, from about 50 nm to about 1000 µm, from about 100 nm to about 750 µm, from about 250 nm to about 500 µm, or from about 500 nm to about 500 µm.

The length of the microneedle body can vary from micrometers to centimeters, depending on a number of factors, e.g., but not limited to, types of tissue targeted for administration, required penetration depths, lengths of the uninserted portion of a microneedle, and methods of applying microneedles across or into a biological barrier. By way of example only, if a microneedle is required to reach into a few centimeters of an organ tissue (e.g., heart tissue) during surgery, the microneedle can be of several centimeters long. In such embodiments, the microneedle can be further secured to an applicator or a device for facilitating the penetration of the microneedle into the organ tissue (e.g., heart tissue). Thus, some embodiments of the microneedles described herein can have a length of about 0.5 cm to about 10 cm, about 1 cm to about 8 cm, or about 2 cm to about 6 cm.

In some embodiments, the length of microneedle body can vary from about 10 µm to about 5000 µm, from about 50 µm to about 2500 µm, from about 100 µm to about 1500 µm, from about 150 µm to about 1000 µm, or from about 200 µm to about 800 µm. In some embodiments, the length of microneedle body can vary from about 200 µm to about 800 µm. By way of example, some embodiments of the microneedles described herein can be used for skin penetration. The skin's outermost barrier, the stratum corneum, is generally about 10 µm to 20 µm thick, and covers the viable epidermis, which is about 50 µm to 100 µm thick. The epidermis is avascular, but it hosts Langerhan's cells (immature myeloid dendritic cells) which can be, for example, relevant in inducing an immune response, e.g., immunization. Below these skin layers, the dermis is about 1 mm to 2 mm thick and houses a rich capillary bed, which can be a useful target for systemic delivery of an active agent. The robust mechanical properties of silk fibroin allow construction of microneedles that penetrate the skin to any appropriate depth. For example, the length of microneedles can be constructed long enough to deliver an active agent to the viable epidermis (about 10 µm to 120 µm below the skin surface), e.g., to induce an immune response. In some embodiments, the length of microneedles can be constructed long enough to deliver an active agent to the dermis (about 60 µm to 2.1 mm below the skin surface). An ordinary artisan can adjust the microneedle length for a number of factors, including, without limitations, tissue thickness, e.g., skin thickness, (as a function of age, gender, location on body, species (animals), drug delivery profile (e.g., fast-long needle vs. slow-short needle; fast—minimal β-sheet structure vs. slow—maximum β-sheet structure), diffusion properties of active agents (e.g., ionic charge, molecule weight, shape), or any combinations thereof. A microneedle length can range between about 50 µm to about 700 µm, depending on the tissue targeted for administration. In some embodiments, devices with individual microneedles ranging in sizes from 15 µm to 300 µm can be fabricated with silk fibroin.

Accordingly, the length of the microneedle body can be selected and constructed for each particular application. In some embodiments, the length of the microneedle body can further comprise an uninserted portion, i.e. a portion of the microneedle that is not generally involved in tissue penetration. In those embodiments, the length of the microneedle body can comprise an insertion length (a portion of a microneedle that can penetrate into or across a biological barrier) and an uninserted length. The uninserted length can depend on applications and/or particular device designs and configurations (e.g., a microneedle adaptor or a syringe that holds a microneedle).

Advantageously, the silk-based microneedles or microneedle devices can be entirely biocompatible and fully or partially biodegradable and/or bioerodible. The term "biocompatible" refers in general to materials that not harmful to the environment or the subject: the environment can be an in vivo environment or an environment outside the body, for example, in a crop field, and environmental chemistries can vary among naturally occurring environments. The term "biodegradable" refers in general to materials that have a chemical structure that may be altered by common environmental chemistries (e.g., enzymes, pH, and naturally-occurring compounds) to yield elements or simple chemical structures that may be resorbed by the environment, including the environment within a subject (e.g., a human), without harm thereto. Biodegradable materials may also be bioerodible, in that they undergo physical loss as well as chemical change. For example, biodegradable materials may be broken down into elements or chemical structures, whereas bioerodible materials may be broken down (e.g., chain scission) at a macroscopic level with chemical structures that remain largely intact. Thus, the silk-based microneedles of the present invention need not be removed from a subject, because they are biocompatible and capable of degrading or eroding into materials or components that are not harmful to the subject. Additionally, silk fibroin can be prepared in an all-aqueous process, further expanding its compatibility with biologics and the environment.

Active Agents and Stabilization Thereof

In some embodiments, the silk fibroin microneedles of the present invention can comprise at least one active agent. The amount of active agents distributed in the microneedles described herein can vary from picogram levels to milligram levels, depending on the size of microneedles and/or encapsulation efficiency. Non-limiting examples of active agents include organic materials such as horseradish peroxidase, phenolsulfonphthalein, nucleotides, nucleic acids (e.g., oligonucleotides, polynucleotides, siRNA, shRNA), aptamers, antibodies or portions thereof (e.g., antibody-like molecules), hormones (e.g., insulin, testosterone), growth factors, enzymes (e.g., peroxidase, lipase, amylase, organophosphate dehydrogenase, ligases, restriction endonucleases, ribonucleases, RNA or DNA polymerases, glucose oxidase, lactase), cells (e.g., red blood cells, stem cells), bacteria or viruses, other proteins or peptides, small molecules (e.g., drugs, dyes, amino acids, vitamins, antioxidants), lipids, carbohydrates, chromophores, light emitting organic compounds (such as luciferin, carotenes) and light emitting inorganic compounds (e.g., chemical dyes and/or contrast enhancing agents such as indocyanine green), immunogenic substances such as vaccines, antibiotics, antifungal agents, antiviral agents, therapeutic agents, diagnostic agents or pro-drugs, analogs or combinations of any of the foregoing. See, e.g., WO 2011/006133, Bioengineered Silk Protein-Based Nucleic Acid Delivery Systems; WO 2010/141133, Silk Fibroin Systems for Antibiotic Delivery; WO 2009/140588, Silk Polymer-Based Adenosine Release: Therapeutic Potential for Epilepsy; WO 2008/118133, Silk Microspheres for Encapsulation & Controlled Release; WO 2005/123114, Silk-Based Drug Delivery System; U.S. Ser. No. 61/477,737, Compositions and Methods for Stabilization of Active Agents, the contents of which are incorporated herein by reference in their entirety.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "nucleic acids" used herein refers to polynucleotides such as deoxyribonucleic acid (DNA), and, where appropriate, ribonucleic acid (RNA), polymers thereof in either single- or double-stranded form. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The term "nucleic acid" should also be understood to include, as equivalents, derivatives, variants and analogs of either RNA or DNA made from nucleotide analogs, and, single (sense or antisense) and double-stranded polynucleotides.

The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include kinases, dehydrogenases, oxidoreductases, GTPases, carboxyl transferases, acyl transferases, decarboxylases, transaminases, racemases, methyl transferases, formyl transferases, and α-ketodecarboxylases.

The term "vaccines" as used herein refers to any preparation of killed microorganisms, live attenuated organisms, subunit antigens, toxoid antigens, conjugate antigens or other type of antigenic molecule that when introduced into a subjects body produces immunity to a specific disease by causing the activation of the immune system, antibody formation, and/or creating of a T-cell and/or B-cell response. Generally vaccines against microorganisms are directed toward at least part of a virus, bacteria, parasite, mycoplasma, or other infectious agent.

Examples of vaccine products that can be included in the microneedles described herein include, but are not limited to, BIOTHRAX® (anthrax vaccine adsorbed, Emergent Biosolutions, Rockville, Md.); TICE® BCG Live (Bacillus Calmette-Guérin for intravesical use, Organon Tekina Corp. LLC, Durham, N.C.); MYCOBAX® BCG Live (Sanofi Pasteur Inc); DAPTACEL® (diphtheria and tetanus toxoids and acellular pertussis [DTaP] vaccine adsorbed, Sanofi Pasteur Inc.); INFANRIX® (DTaP vaccine adsorbed, GlaxoSmithKline); TRIPEDIA® (DTaP vaccine, Sanofi Pasteur); TRIHIBIT® (DTaP/Hib #, sanofi pasteur); KINRIX® (diphtheria and tetanus toxoids, acellular pertussis adsorbed and inactivated poliovirus vaccine, GlaxoSmithKline); PEDIARIX® (DTaP-HepB-IPV, GlaxoSmithKline); PENTACEL® (diphtheria and tetanus toxoids and acellular pertussis adsorbed, inactivated poliovirus and *Haemophilus* b conjugate [tetanus toxoid conjugate] vaccine, sanofi pasteur); Diphtheria and Tetanus Toxoids, adsorbed (for pediatric use, Sanofi Pasteur); DECAVAC® (diphtheria and tetanus toxoids adsorbed, for adult use, Sanofi Pasteur); ACTHIB® (*Haemophilus* b tetanus toxoid conjugate vaccine, Sanofi Pasteur); PEDVAXHIB® (Hib vaccine, Merck); Hiberix (*Haemophilus* b tetanus toxoid conjugate vaccine, booster dose, GlaxoSmithKline); COMVAX® (Hepatitis B-Hib vaccine, Merck); HAVRIX® (Hepatitis A vaccine, pediatric, GlaxoSmithKline); VAQTA® (Hepatitis A vaccine, pediatric, Merck); ENGERIX-B® (Hep B, pediatric, adolescent, GlaxoSmithKline); RECOMBIVAX HB® (hepatitis B vaccine, Merck); TWINRIX® (HepA/HepB vaccine, 18 years and up, GlaxoSmithKline); CERVARIX® (human papillomavirus bivalent [types 16 and 18] vaccine, recombinant, GlaxoSmithKline); GARDASIL® (human papillomavirus bivalent [types 6, 11, 16 and 18] vaccine, recombinant, Merck); AFLURIA® (Influenza vaccine, 18 years and up, CSL); AGRIFLU™ (influenza virus vaccine for intramuscular injection, Novartis Vaccines); FLUARIX® (Influenza vaccine, 18 years and up, GaxoSmithKline); FLULAVAL® (Influenza vaccine, 18 years and up, GaxoSmithKline); FLUVIRIN® (Influenza vaccine, 4 years and up, Novartis Vaccine); FLUZONE® (Influenza vaccine, 6 months and up, Sanofi Pasteur); FLUMIST® (Influenza vaccine, 2 years and up, MedImmune); IPOL® (e-IPV polio vaccine, sanofi Pasteur); JE VAX® (Japanese encephalitis virus vaccine inactivated, BIKEN, Japan); IXIARO® (Japanese encephalitis virus vaccine inactivated, Novarits); MENACTRA® (Meningococcal [Groups A, C, Y and W-135] and diphtheria vaccine, Sanofi Pasteur); MENOMUNE®-A/C/Y/W-135 (Meningococcal polysaccharide vaccine, sanofi pasteur); MMRII® (MMR vaccine, Merck); MENVEO® (Meningococcal [Groups A, C, Y and W-135] oligosaccharide diphtheria CRM197 conjugate vaccine, Novartis Vaccines); PROQUAD® (MMR and varicella vaccine, Merck); PNEUMOVAX 23® (pneumococcal polysaccharide vaccine, Merck); PREVNAR® (pneumococcal vaccine, 7-valent, Wyeth/Lederle); PREVNAR-13® (pneumococcal vaccine, 13-valent, Wyeth/Lederle); POLIOVAX™ (poliovirus inactivated, sanofi pasteur); IMOVAX® (Rabies vaccine, Sanofi Pasteur); RABAVERT™ (Rabies vaccine, Chiron); ROTATEQ® (Rotavirus vaccine, live, oral pentavalent, Merck); ROTARIX® (Rotavirus, live, oral vaccine, GlaxoSmithKline); DECAVAC™ (tetanus and diphtheria toxoids vaccine, sanofi pasteur); Td (generic) (tetanus and diphtheria toxoids, adsorbed, Massachusetts Biol. Labs); TYPHIMVI® (typhoid Vi polysaccharide vaccine, Sanofi Pasteur); ADACEL® (tetanus toxoid, reduced diphtheria toxoid and acellular pertussis, sanofi pasteur); BOOSTRIX® (tetanus toxoid, reduced diphtheria toxoid and acellular pertussis, GlaxoSmithKline); VIVOTIF® (typhoid vaccine live oral Ty21a, Berna Biotech); ACAM2000™ (Smallpox (vaccinia) vaccine, live, Acambis, Inc.); DRYVAX® (Smallpox (vaccinia) vaccine); VARIVAX® (varicella [live] vaccine, Merck); YF-VAX® (Yellow fever vaccine, Sanofi Pasteur); ZOSTAVAX® (Varicella zoster, Merck); or combinations thereof. Any vaccine products listed in database of Center for Disease Control and Prevention (CDC) can also be included in the compositions described herein.

In some embodiments, animal vaccines such as canine and feline vaccines can also be included in the microneedles described herein. Examples of animal vaccines include, but are not limited to, DURAMUNE® MAX 5 (5-way vaccine: Canine Distemper, Infectious Canine Hepatitis, Adenovirus Type 2, Parainfluenza, and Parvovirus, Fort Dodge); NEO PAR® (parvovirus, Neo Tech); VANGUARD® PLUS 5 (Canine Distemper, Adenovirus Type 1 and 2, Parainfluenza and Parvovirus; Pfizer); BRONCHI-SHIELD® III (Canine Parainfluenza; Fort Dodge); and ECLIPSE® 4 (feline rhinotracheitis, calici, and panleukopenia viruses and *Chlamydia psittaci*, Schering-Plough/Intervet). Any commercially available animal vaccines can be included in the microneedles described herein.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nor-mucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (Pluckthun, The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "bacteria" as used herein is intended to encompass all variants of bacteria, for example, prokaryotic organisms and cyanobacteria. Bacteria are small (typical linear dimensions of around 1 m), non-compartmentalized, with circular DNA and ribosomes of 70S.

The term "antibiotics" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, and sulfamethoxazole.

The term "cells" used herein refers to any cell, prokaryotic or eukaryotic, including plant, yeast, worm, insect and mammalian. Mammalian cells include, without limitation; primate, human and a cell from any animal of interest, including without limitation; mouse, hamster, rabbit, dog, cat, domestic animals, such as equine, bovine, murine, ovine, canine, feline, etc. The cells may be a wide variety of tissue types without limitation such as; hematopoietic, neural, mesenchymal, cutaneous, mucosal, stromal, muscle spleen, reticuloendothelial, epithelial, endothelial, hepatic, kidney, gastrointestinal, pulmonary, T-cells etc. Stem cells, embryonic stem (ES) cells, ES-derived cells and stem cell progenitors are also included, including without limitation, hematopoeitic, neural, stromal, muscle, cardiovascular, hepatic, pulmonary, gastrointestinal stem cells, etc. Yeast cells may also be used as cells in this invention. In some embodiments, the cells can be ex vivo or cultured cells, e.g. in vitro. For example, for ex vivo cells, cells can be obtained from a subject, where the subject is healthy and/or affected with a disease. Cells can be obtained, as a non-limiting example, by biopsy or other surgical means know to those skilled in the art.

As used herein, the term "viruses" refers to an infectious agent composed of a nucleic acid encapsidated in a protein. Such infectious agents are incapable of autonomous replication (i.e., replication requires the use of the host cell's machinery). Viral genomes can be single-stranded (ss) or double-stranded (ds), RNA or DNA, and can or cannot use reverse transcriptase (RT). Additionally, ssRNA viruses can be either sense (+) or antisense (−). Exemplary viruses include, but are not limited to, dsDNA viruses (e.g. Adenoviruses, Herpesviruses, Poxviruses), ssDNA viruses (e.g. Parvoviruses), dsRNA viruses (e.g. Reoviruses), (+)ssRNA viruses (e.g. Picornaviruses, Togaviruses), (−)ssRNA viruses (e.g. Orthomyxoviruses, Rhabdoviruses), ssRNA-RT viruses, i.e., (+)sense RNA with DNA intermediate in life-cycle (e.g. Retroviruses), and dsDNA-RT viruses (e.g. Hepadnaviruses). In some embodiments, viruses can also include wild-type (natural) viruses, killed viruses, live attenuated viruses, modified viruses, recombinant viruses or any combinations thereof. Other examples of viruses include, but are not limited to, enveloped viruses, respiratory syncytial viruses, non-enveloped viruses, bacteriophages, recombinant viruses, and viral vectors. The term "bacteriophages" as used herein refers to viruses that infect bacteria.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

In some embodiments, the therapeutic agent can include pain medications. Examples of pain medications include, but are not limited to, acetaminophen, non-steroidal anti-inflammatory medications (NSAIDs), corticosteroids (e.g., without limitations, MEDROL®, PREDNISONE® or cortisone); narcotics; anti-convulsants (e.g., without limitations, NEU- RONTIN® (Gabapentin), LYRICA® (Pregabalin)); local anesthetics (e.g., LIDODERM®), and any combinations thereof.

Exemplary NSAIDs that can be included in some embodiments of the microneedles provided herein include, but not limited to, ibuprofen, naproxin, aspirin, fenoprofen (NALFON), flurbiprofen (ANSAID®), ketoprofen (ORUVAIL®), oxaprozin (DAYPRO®), diclofenac sodium (VOLTAREN®, VOLTAREN-XR®, CATAFLAM®), etodolac (LODINE®), indomethacin (INDOCIN®, INDOCIN-SR®), ketorolac (TORADOL®), sulindac (CLINORIL®), tolmetin (TOLECTIN®), meclofenamate (MECLOMEN®), mefenamic acid (PONSTEL®), nabumetone (RELAFEN®), piroxicam (FELDENE®) and COX-2 inhibitors such as CELEBREX®.

In some embodiments, the pain medications can include acetaminophen combinations (e.g., acetaminophen with a narcotic) such as acetaminophen with codeine (e.g., but not limited to, TYLENOL® with Codeine, CAPITAL® and Codeine, Phenaphen with Codeine); acetaminophen with hydrocodone (e.g., but not limited to, ANEXSIA®; ANODYNOS-DHC®; BANCAP HC®; CO-GESIC®; DOLACET®; DUOCET™; HYDROCET®; HYDROGESIC®; HY—PHEN®; LORCET®; LORCET®-HD; LORCET® PLUS; LORTAB®; MARGESIC® H; MEDIPAIN 5®; NORCO®; STAGESIC®; T-GESIC®; VICODIN®; VICODIN® ES; VICODIN® HP; ZYDONE®); and acetaminophen with oxycodone (PERCOCET®, ROXICET®, ENDOCET®, ROXILOX®, TYLOX®).

A "diagnostic agent" is any chemical moiety that can be used for diagnosis. For example, diagnostic agents include imaging agents containing radioisotopes such as indium or technetium; contrast agents or dyes containing iodine, gadolinium or cyanine; enzymes such as horse radish peroxidase, GFP, alkaline phosphatase, or β-galactosidase; fluorescent substances such as europium derivatives; luminescent substances such as N-methylacrydium derivatives or the like.

The term "antifungal agent" as used herein refers to a substance capable of inhibiting or preventing the growth, viability and/or reproduction of a fungal cell. In some embodiments, antifungal agents include those capable of preventing or treating a fungal infection in an animal or plant. An antifungal agent can be a broad spectrum antifungal agent or an antifungal agent specific to one or more particular species of fungus. Non-limiting examples of antifungal agents include ergosterol synthesis inhibitors such as azoles (e.g., imidazoles and triazoles) and phenpropimorph, terbinafine, ketoconazole, itroconazole, fluconazole, voriconazole, posaconazole, ravuconazole and miconazole.

The term "antiviral agent" as used herein includes any agent used for treating viral infections, destroying or retarding the growth and reproduction of viruses, and/or retarding viral infections, e.g., by interfering with a virus's ability to enter a host cell and replicate itself with the host cell's DNA; by reducing the virus's attachment or entry into the cell; by retarding replication; and/or by preventing the virus from shedding the protein coat that surrounds the viral DNA. Without limitations, exemplary antiviral agents include ribavirin, acyclovir, oseltamivir and zanamivir, amantadine and rimantadine.

As used herein, the term "hormones" generally refers to naturally or non-naturally occurring hormones, analogues and mimics thereof. In certain embodiments, the term "hormones" refers to any hormones used in therapeutic treatment, e.g., growth hormone treatment. As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or variant produced by means of recombinant DNA technology, including somatrem, somatotropin, and somatropin. In one embodiment, hormones include insulin.

In certain embodiments, the term "active agent" is used in reference to any molecule, compound or composition, bioactivity of which is desired to be stabilized when such molecule, compound, or composition is subjected to a specified condition, which inhibits or reduces the bioactivity of the active agent, for a period of time. Such conditions can include, but are not limited to, a state-changing cycle, temperatures, air pressures, humidity, and light exposure. In one embodiment, the state-changing cycle is a freeze-thaw cycle. In accordance with the invention, the bioactivity of at least one active agent can be maintained within silk fibroin-based microneedles comprising the active agent.

When the silk fibroin-based microneedles loaded with at least one active agent (referred as "active agent-loaded microneedles") are subjected to a state-changing cycle and/or are maintained for a period of time under a specified condition, the active agent can retain at least about 30% of its original bioactivity e.g., at least about 40%, at least about 50%, at least about 60%, at least about 70%, at least about 80%, at least about 90%, at least about 95% of the original bioactivity or higher. Stated another way, the stability of an active agent in silk fibroin-based microneedles (i.e., the ability of an active agent to retain its bioactivity (e.g., at least about 30% of its original bioactivity) in silk fibroin-based microneedles) can be increased by at least about 30%, at least about 40%, at least about 50%, at least about 60%, at least about 70%, at least about 80%, at least about 90%, at least about 95%, relative to the stability of an active agent in non-silk fibroin-based microneedles.

The active agent-loaded microneedles described herein can be maintained at any temperatures or at a manufacturer's recommended temperature specified for an active agent. In some embodiments, the active agent-loaded microneedles can be maintained in liquid nitrogen or in dry ice. In some embodiments, the active agent-loaded microneedles can be maintained, for example, between about −80° C. and about −20° C., inclusive, or between about −20° C. and about 0° C., inclusive. In some embodiments, the active agent-loaded microneedles can be maintained at a temperature above 0° C. In those embodiments, the active agent-loaded microneedles can be maintained at a temperature from about 0° C. to about an ambient temperature. As used herein, the term "ambient temperature" is used to describe a surrounding temperature at which the active agent-loaded microneedles described herein are maintained and it includes temperatures between 0° C. and 60° C., between 0° C. and 50° C., or between 0° C. and 40° C. In some embodiments, the ambient temperature is the fridge temperature (e.g., between 0° C. and 15° C., inclusive). In some embodiments, the ambient temperature is about the body temperature of a subject (e.g., between 36° C. and 38° C., inclusive, for a human subject, or a higher or lower body temperature range for other animals). In some embodiments, the ambient temperature is the room temperature, e.g., between 20° C. and 35° C., and it can vary with geographical conditions. For example, the room temperature in warm-climate regions, e.g., Africa, can be generally warmer than that in cool-climate regions, e.g., the United States or United Kingdom.

The active agent-loaded microneedles described herein can be maintained for any period of time, e.g., hours, days, weeks, months or years. In some embodiments, the active agent-loaded microneedles described herein can be maintained for at least about 3 hours, at least about 6 hours, at least about 9 hours, at least about 12 hours, at least about 24 hours or longer. In some embodiments, the active agent-loaded microneedles described herein can be maintained for at least about 1 day, at least about 2 days, at least about 3 days, at least about 4 days, at least about 5 days, at least about 6 days, at least about 7 days or longer. In some embodiments, the active agent-loaded microneedles described herein can be maintained for at least about 1 week, at least about 2 weeks, at least about 3 weeks, at least about 4 weeks or longer. In some embodiments, the active agent-loaded microneedles described herein can be maintained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months or longer.

Microneedle Devices

Another aspect provided herein is a microneedle device comprising a substrate and one or more silk fibroin microneedles described herein integrated or attached to the substrate and extending from the substrate, wherein each silk fibroin microneedle comprises a base and a penetrating tip. In some embodiments, the microneedle device can comprise a substrate and a silk fibroin microneedle. In some embodiments, the microneedle device can comprise a substrate and at least 2, at least 3, at least 4, at least 5, at least 6, at least 7, at least 8, at least 9, at least 10, at least 15, at least 20, at least 25, at least 30, at least 40, at least 50, at least 60, at least 70, at least 80, at least 90, at least 100 or more microneedles.

Figure 2:
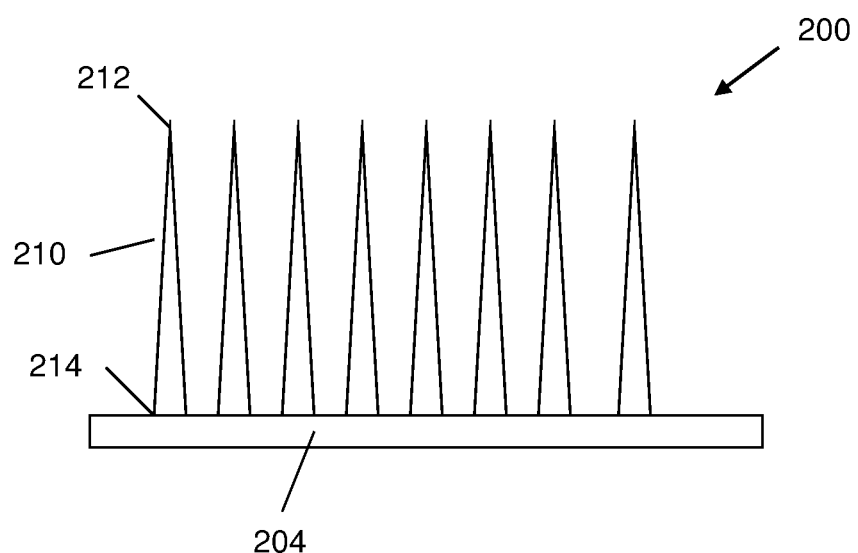
FIG. 2 is a diagrammatic view of a microneedle device, comprising a plurality of silk fibroin microneedles projected from a substrate, according to one or more embodiments of the invention.
Figure 3A:
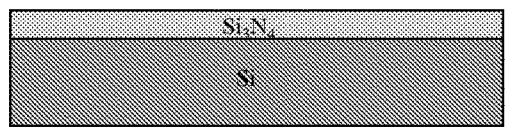
Figure 3B:
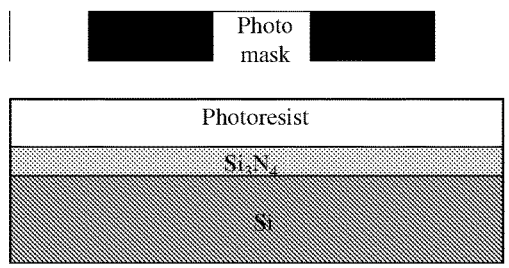
Figure 3C:
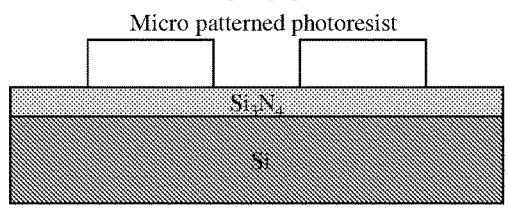
Figure 3D:
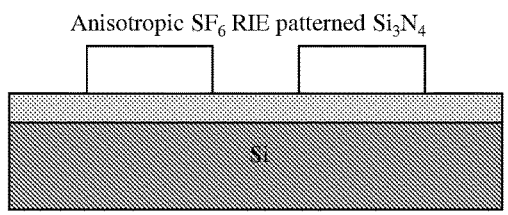
Figure 3E:
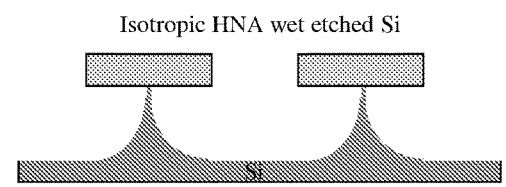
Figure 3F:
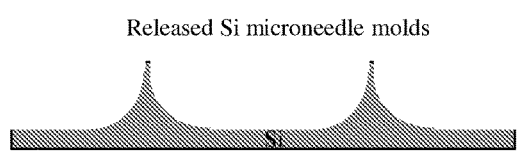
Figure 3G:
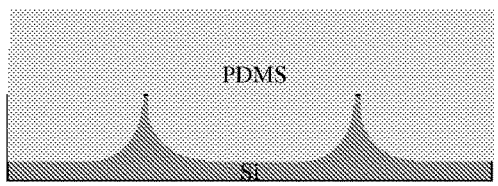
Figure 3G:
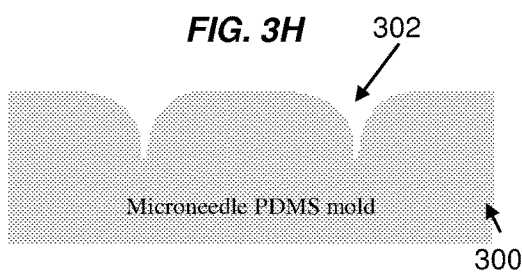
Figure 3I:
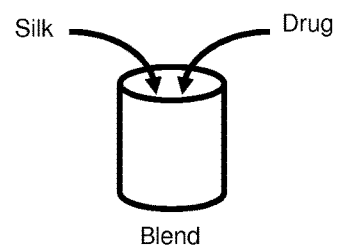
Figure 3J:
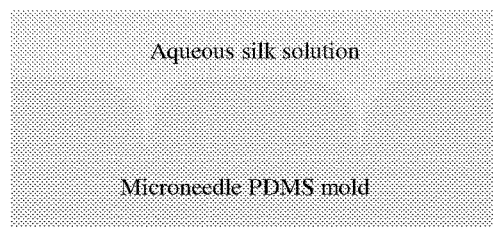
Figure 3K:
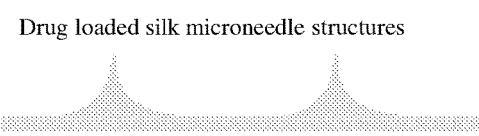

FIG. 2 shows a diagram of at least a portion of a microneedle device 200 according to one or more embodiments of the present invention. The microneedle device 200 of the present invention can be formed from a silk fibroin material that is highly biocompatible and easy to manufacture. The microneedle device 200 includes a substrate 204 and a plurality of silk fibroin microneedles 210 projecting from the substrate 204. The basic geometry requirements (including aspect ratio, base diameter, and taper profile) of the microneedles can be dictated by the microneedle function, i.e., penetrating a biological barrier, maintaining geometry during penetration, and reaching required penetration depth. In some embodiments, the silk fibroin microneedles 210 can be integrally formed and extended from the substrate 204. In some embodiments, the silk fibroin microneedles 210 can be pre-formed and then attached to a separate substrate 204. The silk fibroin microneedles can include one or more active agents to be applied into or across a biological barrier at a treatment site. As described herein, each microneedle includes a microneedle body 210 extending from a base 214 to a penetrating tip 212, e.g., by a predefined distance (indicated by the length of the microneedle body). The penetrating tips 212 as described herein can have a dimension (e.g., diameter) of any size, based upon various factors, e.g., types of biological barrier to be penetrated, microneedle design requirement (e.g., aspect ratio), conditions of fabrication process, and/or uses' preferences or applications. In various embodiments, the penetrating tips 212 can have a dimension (e.g., diameter) of any size, e.g., in a nanometer or micrometer range. In some embodiments, the penetrating tips 212 can have a dimension (e.g., diameter) ranging from about 50 nm to about 50 µm. In other embodiments, the penetrating tips 212 can have a dimension (e.g., diameter) greater than 50 µm. The length of the microneedle body 210 can be selected to position the penetrating tips 212 at a predefined distance from the base 214 to provide tissue penetration and active agent application to a predefined depth. The base 214 can be mounted to a substrate 204 or formed as part of the substrate 204, for example, in the form of a film. The shape and diameter of the microneedle body can be selected according to the desired mode of treatment and the characteristics of the treatment site.

Each microneedle present on the microneedle device need not have the same microneedle length. In some embodiments, each microneedle on the microneedle device can have the same microneedle body length. In alternative embodiments, the microneedles on the microneedle device can have different microneedle body lengths. Thus, a predefined profile of constant or varying microneedle depth penetrations can be provided in a single microneedle device. In some embodiments, the body length of each microneedle can be tuned to adjust for the curvature of a surface.

Figure 8A:
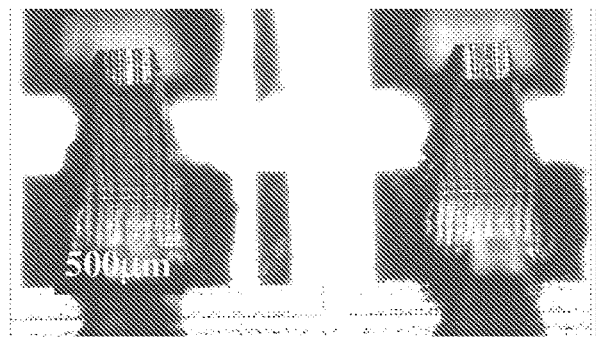
FIGS. 8A-8F show images of an Al molding master and exemplary silk fibroin microneedles.
Figure 8B:
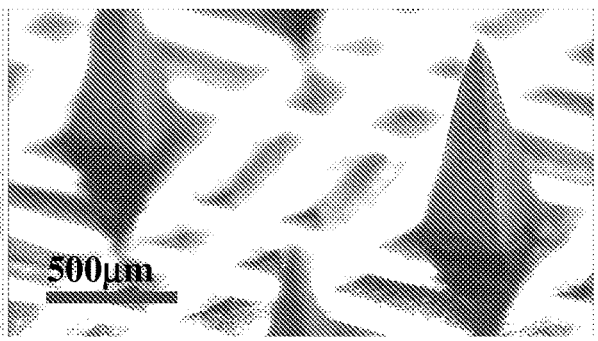
Figure 8C:
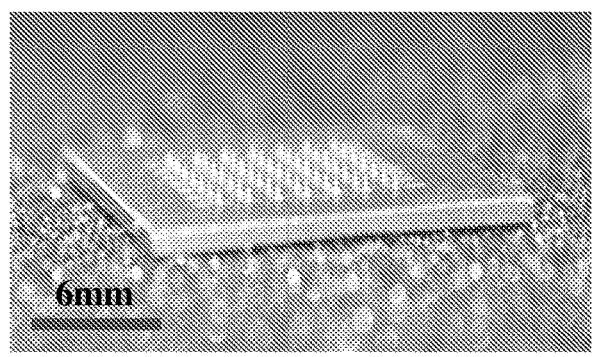
Figure 8D:
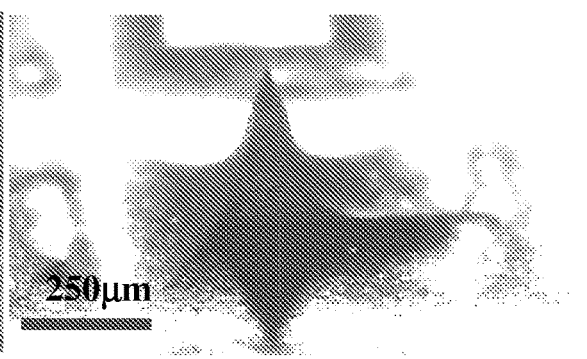
Figure 8E:
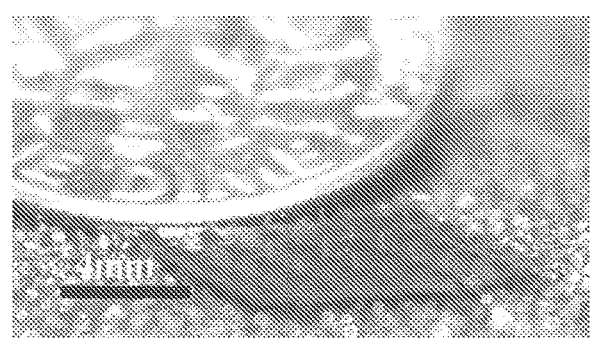
Figure 8F:
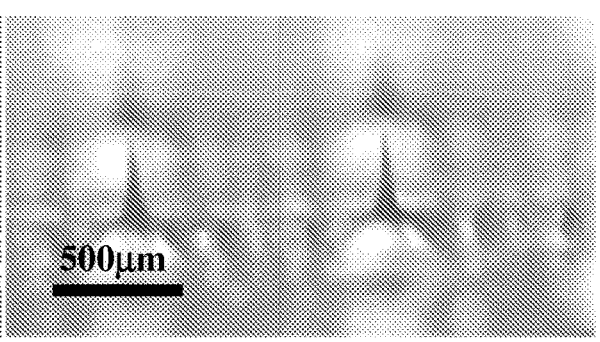

A plurality of microneedles can be arranged in a random, pseudo-random or predefined pattern, such as an array as shown in FIG. 8E. The distance between the microneedles and the arrangement of the plurality of microneedles can be selected according to the desired mode of treatment and characteristics of the treatment site. For example, in some embodiments, a sub-population of microneedles can be arranged closely together as a group, e.g., to increase the amount of active agent delivered to a target spot.

The microneedles can be oriented perpendicular or at an angle to the substrate. In some embodiments, the microneedles can be oriented perpendicular to the substrate. In such embodiments, a larger density of microneedles per unit area of substrate can be provided.

Substrate:

The substrate of the microneedle device can be constructed from a variety of materials, including metals, ceramics, semiconductors, organics, polymers, and any composites thereof. The substrate includes the base substrate to which the microneedles are attached or integrally formed. The substrate can then be adapted to fit a Luer-Lock syringe or other conventionally used drug delivery device that currently uses hypodermic needles as the barrier penetration method.

In some embodiments of the device, the substrate can comprise one or more biocompatible polymers. By the term "biocompatible polymer" meant is a polymeric material which when in contact with a human body does not provoke an adverse response in the subject. Examples of biocompatible polymers include, but are not limited to, silicone and silicone-based polymers; polytetrafluoroethylene (PTFE); a natural or synthetic hydrogel; polyurethane; polysulfone; cellulose; polyethylene; polypropylene; polyamide; polyester; polymethylmethacrylate, polylactic acid (PLA), polyglycolic acid (PGA), poly(lactic-co-glycolic acid) (PLGA), any art-recognized biocompatible polymers, and any combinations thereof.

In some embodiments of the device, the substrate can comprise one or more biodegradable polymers, e.g., but not limited to, poly(lactide)s, poly(glycolide)s, poly(lactide-co-glycolide)s, polyanhydrides, polyorthoesters, polyetheresters, polycarpolactones, polyesteramides, poly(butyric acid)s, poly(valeric acid)s, polyhydroxyalkanoates, degradable polyurethanes, any copolymers thereof, and any blends thereof.

In some embodiments of the device, the substrate can be formed from any flexible material. In such embodiments, the substrate can be sufficiently flexible to conform to a surface upon contact with the surface, e.g., a tissue or an organ surface, while allowing the microneedles to penetrate the tissue to the desired depth. In one embodiment, the flexible substrate comprises a silk fibroin film integrated with silk fibroin microneedles. In alternative embodiments, the substrate can be any rigid material.

The surface of the substrate from which the microneedles extend can be a substantially flat surface, a curved surface, a wavy surface or any combinations thereof. In some embodiments, the surface of the substrate from which the microneedles extend can be configured to have a curvature profile similar to that of a target surface to be penetrated.

The substrate can be of any shape and/or any dimension determined from, for example, design of the microneedle device, area/shape of a target site to be treated, and/or size of microneedle applicators. In some embodiments, the shape and dimension of the substrate can be configured to fit any applicator that currently uses hypodermic needles as the barrier penetration method (e.g., syringes), any microinjection equipment, any microneedle holders, any microneedle administration or applicator devices, any microneedle array applicator devices, and/or microneedle array cartridge systems. Non-limiting examples of the microneedle or microneedle array injectors or applicators include the ones described in U.S. patent application Nos.: US 2008/0183144; US 2003/0208167; US 2010/0256597; and U.S. Pat. Nos. 6,743,211; and 7,842,008.

In some embodiments, the substrate can comprise at least one active agent distributed therein. In some embodiments, the substrate can comprise no active agent described herein.

Methods of Producing Microneedles and Microneedle Devices Described Herein

The methods used in fabrication of any embodiments of the microneedle and/or microneedle devices described herein can vary with the materials used, and include soft lithography methods, microassembly, micro shaping, bulk micromachining methods, surface micro-machining methods, standard lithographic methods, wet etching, reactive ion etching, plasma etching, stereolithography and laser chemical three-dimensional writing methods, solid-object printing, machining, modular assembly methods, micromolding, replica molding methods, injection molding methods, hot molding methods, laser ablation methods, any microfabrication methods, combinations of methods, and other methods known in the art for fabrication of microneedles, including, but not limited to, the methods described in U.S. Pat. No. 6,503,231; U.S. patent application Nos.: US 2003/0208167, and US 2009/0182306; and Henry et al., "Micromachined Needled for the Transdermal Delivery of Drugs," Micro Electro Mechanical Systems, Heidelberg, Germany, p. 494-498 (Jan. 26-29, 1998).

FIGS. 3A-3K and 7A-7F show examples of fabricating one or more embodiments of the microneedles described herein by molding. In one embodiment, the method includes providing a mold having one or a plurality of microdepressions, each of which defines the surface of a microneedle (e.g., microdepressions 302, 702 of a PDMS mold 300, 700), filling at least one microdepression with a silk fibroin solution; and molding the silk fibroin, thereby forming microneedles. The nature of silk fibroin allows for much finer, yet easily reproducible, molded microneedles compared with other polymers.

Silk Fibroin:

Silk fibroin is a particularly appealing biopolymer candidate to be used for embodiments of the invention, e.g., because of its all aqueous processing (Sofia et al., 54 J. Biomed. Mater. Res. 139 (2001); Perry et al., 20 Adv. Mater. 3070-72 (2008)), relatively easy functionalization (Murphy et al., 29 Biomat. 2829-38 (2008)), and biocompatibility (Santin et al., 46 J. Biomed. Mater. Res. 382-9 (1999)). For example, silk has been approved by U.S. Food and Drug Administration as a tissue engineering scaffold in human implants. See Altman et al., 24 Biomaterials: 401 (2003).

As used herein, the term "silk fibroin" includes silkworm fibroin and insect or spider silk protein. See e.g., Lucas et al., 13 Adv. Protein Chem. 107 (1958). Any type of silk fibroin may be used according to aspects of the present invention. Silk fibroin produced by silkworms, such as *Bombyx mori*, is the most common and represents an earth-friendly, renewable resource. For instance, silk fibroin used in a silk film may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used. In some embodiments of any aspects described herein, the silk fibroin used for fabrication of the microneedles can be regenerated silk fibroin. In some embodiments, silk fibroin can be sericin-depleted, e.g., using the method described in the Examples.

The aqueous silk fibroin solution used for making microneedles and/or microneedle devices described herein can be prepared using any techniques known in the art. The concentration of silk fibroin in solutions used to embed or carry active agent can be suited to the particular active agent and/or pre-determined release profile. In some embodiments, the silk fibroin solution for making the microneedles and/or microneedle devices described herein can vary from about 4% (w/v) to about 20% (w/v), inclusive. In some embodiments, the silk fibroin solution can vary from about 6% (w/v) to about 8% (w/v). Suitable processes for preparing silk fibroin solution are disclosed, for example, in U.S. patent application Ser. No. 11/247,358; WO/2005/012606; and WO/2008/127401. A micro-filtration step can be used herein. For example, the prepared silk fibroin solution can be processed further, e.g., by centrifugation and/or syringe based micro-filtration before further processing into silk matrix-based microneedles and/or microneedle devices described herein.

In various embodiments, the silk fibroin can be modified for different applications and desired properties (e.g., modulation of molecule release profile, mechanical property of microneedles, and stabilization of active agents). One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. patent application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. Additionally, the silk fibroin matrix can be combined with a chemical, such as glycerol, that, e.g., affects flexibility of the matrix. See, e.g., WO 2010/042798, Modified Silk films Containing Glycerol.

In some embodiments, the silk fibroin can be also mixed with other biocompatible and/or biodegradable polymers to form mixed polymer microneedles comprising silk fibroin. One or more biocompatible and/or biodegradable polymers (e.g., two or more biocompatible polymers) can be added to the aqueous solution together with the silk fibroin. The biocompatible polymer that can be used herein include, but are not limited to, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid and other biocompatible and/or biodegradable polymers. See, e.g., International Application Nos.: WO 04/062697; WO 05/012606. The microneedles can be biodegradable, bioerodible or otherwise designed to leave at least a portion of the microneedle in the tissue penetrated.

In some embodiments, at least one active agent described herein can be added to the silk fibroin solution before forming silk fibroin microneedles or microneedle devices described herein. In such embodiments, the active agent can be added to the silk fibroin solution before, during, or after filling the mold, such that the active agent is dispersed in the microneedles.

Bulk-loaded silk fibroin can be used in a straightforward method for preparing such active agent-loaded silk fibroin microneedles. Silk solution can be mixed with the active agent of interest; microneedles of the desired thickness and surface area can be cast, dried, and then treated to produce the desired material properties. The active agent-loaded microneedles or microneedle devices can be used as monolithic, active agent-delivering implants or diagnostic devices. For example, contrast agents such as GFP molecules loaded in silk fibroin-based microneedles and/or microneedle devices can maintain their nonlinear optical properties. Putthanarat et al., 45 Polymer 8451 (2004). Additionally, the diffusion of small molecule pharmaceuticals (5-fluorouracil, vitamin C, resorcinol, sodium phenolsulfonate and benzyltrimethylammonium chloride) through silk fibroin films has been studied, and it was found that permeability was dependent on pH and drug properties. Chen et al., 35 Polymer 2853 (1994). Further, monolithic, bulk-loaded films were prepared from aqueous silk solution containing dextrans of different molecular weights (4 kDa, 10 kDa, 20 kDa, and 40 kDa) and horseradish peroxidase (HRP) and lysozyme (Lys) as model proteins. Release from the films was sustained for approximately 4 weeks, and release behavior was related to film crystallinity and drug properties (including molecular weight and adsorption to the silk). Hofmann et al., 111 J. Contr. Release 219 (2006). Heparin-loaded blended polyurethane-silk films showed heparin release sustained over 24 hours, and exhibited high controllability: release rate and percentage of the cumulative amount of the released heparin could be controlled by adjusting (a) the amount of heparin loaded in the film; (b) the composition ratio of silk fibroin to polyurethane; and (c) the thickness of the film. Liu et al., 63 Mats. Lett. 263 (2009). Accordingly, the active agent can be dispersed homogeneously or heterogeneously within the silk fibroin, dispersed in a gradient, e.g., using the carbodiimide-mediated modification method described in the U.S. Patent Application No. US 2007/0212730.

In alternative embodiments, the microneedles can be formed and then contacted with (e.g., dipped into) at least one active agent such that the exterior surface of the microneedles can be coated with at least one active agent.

Microneedle arrays fabricated from silk protein has been previously disclosed, but they exhibited rapid and uncontrolled burst release [8]. In accordance with embodiments of the invention, silk processing can be used to affect silk fibroin properties including $\beta$-sheet content, solubility, active agent loading capacity, degradation time, and drug permeability. Silk processing options include controlled slow drying (Lu et al., 10 Biomacromolecules 1032 (2009)), water annealing (Jin et al., Water-Stable Silk Films with Reduced $\beta$-Sheet Content, 15 Adv. Funct. Mats. 1241 (2005)), stretching (Demura & Asakura, Immobilization of glucose oxidase with *Bombyx mori* silk fibroin by only stretching treatment and its application to glucose sensor, 33 Biotech & Bioengin. 598 (1989)), compressing, and solvent immersion, including methanol (Hofmann et al., 2006), ethanol (Miyairi et al., 1978), glutaraldehyde (Acharya et al., 2008) and 1-ethyl-3-(3-dimethyl aminopropyl) carbodiimide (EDC) (Bayraktar et al., 2005). In accordance with one embodiment of the invention, silk processing can be used to control the release of an active agent from silk fibroin microneedles structures and devices. In accordance with other embodiments of the invention, other characteristics imparted by processing according to one or more processing options.

Accordingly, the ability to effect silk fibroin structural changes can be harnessed to control not only the mechanical characteristics of the microneedles described herein, but also to control dissolution rates of the needles and/or sustained release profiles of active agents delivered via the microneedles. For example, some embodiments of the silk fibroin microneedles and/or microneedle devices described herein can be further processed to modulate the solubility of silk fibroin microneedles and/or microneedle devices. In some embodiments, the solubility of silk fibroin microneedles and/or microneedle devices described herein can be modulated by effecting a desired level of tertiary structure, e.g., $\beta$-sheet structure. For example, silk fibroin microneedles can be prepared as directed herein, and then treated to adjust the random coil, $\beta$-turns and $\beta$-sheet structures in the fibroin. In such embodiments, the insolubility of silk fibroin in aqueous solution and/or its $\beta$-sheet structure can be induced by a number of methods known in the art, e.g., heat treatment (e.g., water annealing), stretching, methanol or ethanol immersion, and any combinations thereof. For example, in some embodiments, air-dried fibroin microneedles can contain about 10% $\beta$-sheet structure. Methanol treatment can increase the $\beta$-sheet content to above 50% or more. The structure of the fibroin film, regardless of treatment, can be stable for many months in ambient temperatures. In some embodiments, a variety of enzymes can be loaded into silk fibroins at varying concentrations without affecting the silk fibroin structure. In addition, providing a high content of β-sheet structures can be used to render the silk fibroin water-insoluble.

In some embodiments, the silk fibroin microneedles and/or microneedle devices described herein can comprise porous structures, e.g., to modulate the release profiles of active agents into a biological barrier. Methods for generating porous structures within silk fibroin matrix, e.g., freeze-drying, salt-leaching, and gas foaming methods, are well known in the art and have been described in, e.g., U.S. Pat. No. 7,842,780; and US patent application Nos: US 2010/0279112; and US 2010/0279112, the contents of which are incorporated herein by reference in their entirety.

Accordingly, in some embodiments, porous silk fibroin microneedles can be produced by salt-leaching method. See, e.g., U.S. Pat. No. 7,842,780; and US 2010/0279112. The silk fibroin solution can be placed into a microneedle mold, containing water-soluble particles, or porogens, that are insoluble in organic solvents. Alternatively, the porogens can be mixed with the silk polymer solution prior to placement in the mold. The diameter of the particles (porogens) can vary in accordance with the pre-determined pore size. Examples of water-soluble porogens can be used herein include, NaCl, alkali metals, alkali earth metal halides, phosphates, and sulfates, sugar crystals, water-soluble microspheres, polysaccharides and protein microspheres. The dried silk fibroin microneedles or microneedle devices can then be immersed in water or other solvent in which the particles, or porogens are soluble but silk fibroin is insoluble, to remove the particles (porogens), resulting in a porous silk fibroin microneedles or microneedle devices described herein.

In alternative embodiments, porous silk fibroin microneedles can be produced by freeze-drying method. See, e.g., U.S. Pat. No. 7,842,780 and US 2010/0279112. In such embodiments, the silk fibroin solution put in a microneedle mold can be frozen at sub-zero temperatures, e.g., from about −80° C. to about −20° C., for at least about 12 hours, at least about 24 hours, or longer, followed by lyophilization. In one embodiment, the silk fibroin solution can be frozen from one direction. In some embodiments, the silk fibroin solution can contain no salt. In some embodiments, alcohol such as 15%-25% of methanol or propanol can be added to the silk fibroin solution.

In some embodiments, the microneedle can contain a fluidic microchannel therein. The fluidic microchannel can extend from the penetrating tip to the base of the microneedle. In some embodiments where the microneedle is attached to a substrate of the microneedle device described herein, the fluidic microchannel can extend from the penetrating tip of the microneedle to an opposite surface of the substrate. The fluidic microchannel can allow delivery or transport of an active agent, e.g., for fast release and/or a bolus dose of active agent administered to a target site. In some embodiments, the fluidic microchannel can be connected to a separate reservoir, e.g., containing an active agent to be administered. Any methods for microneedle fabrication described herein can be adapted to create a fluidic microchannel within the microneedles described herein. For example, a fluidic microchannel can be etched into pre-formed microneedles, or a positive mold can be adapted to include a fluidic channel. Additional methods for creating microneedles with a fluidic channel include, but not limited to, the methods described in U.S. Pat. No. 6,503,231.

In some embodiments, the microneedles described herein can be coated with at least one layer of a biocompatible and/or biodegradable polymer described herein, e.g., to modulate the rate of active agents released from the microneedles. In such embodiments, the biocompatible and/or biodegradable polymer can comprise at least one active agent.

For some embodiments of producing microneedles and/or microneedle devices described herein by molding, the microdepressions of the microneedle mold can be filled with a silk fibroin solution. In some embodiments, the microdepression can be filled partially with a silk fibroin solution. In some embodiments, the microdepression can be filled completely with a silk fibroin solution. In some embodiments, the microdepression can be filled layer-by-layer with a different silk fibroin solution (e.g., different silk fibroin concentration and/or composition). In some embodiments, the microdepression can be filled layer-by-layer with a silk fibroin solution and a different biocompatible and/or biodegradable polymer, and any blends thereof.

To produce a microneedle device with a substrate, e.g., by molding, the substrate can be formed simultaneously with the molding of the microneedles, e.g., the microneedle mold can be overfilled with a silk fibroin solution so that a layer of silk fibroin solution can be formed above the microneedle mold and subsequently dried into a substrate which is attached to the microneedles and supports the microneedles. In such embodiments, the substrate and microneedles are integrally connected. In alternative embodiments, all or part of the microneedles can be first formed, and then attached or integrated to a separate substrate. For example, in some embodiments, the pre-formed microneedles can be attached to a separate substrate, e.g., with a glue or by welding. In some embodiments, all or part of the microneedles can be first formed in the microneedle mold, followed by a second material formed or molded on top of the microneedles. In some embodiments, at least one additional substrate (e.g., with the same or a different material) can be formed on the surface of the substrate where no microneedles are attached, e.g., by depositing a biopolymer solution over the dried silk fibroin-based microneedle device that still remains in the microneedle mold, and drying the biopolymer solution to form an additional substrate.

In some embodiments, the surface of the substrate to which the microneedles are attached can comprise a biocompatible and/or biodegradable polymer film. In such embodiments, the surface of the substrate to which the microneedles are attached can be coated with a biocompatible and/or biodegradable polymer film, e.g., by depositing a biocompatible and/or biodegradable polymer film on the surface of the substrate, or by causing the microneedles of the microneedle device to penetrate a biocompatible and/or biodegradable polymer film such that the polymer film attaches to the surface of the substrate.

One approach of fabricating the microneedles and/or microneedle devices described herein is molding. The microneedle mold or the microneedle micromold can be produced by any methods known in the art. In one embodiment, as shown in FIGS. 3A-3F, the microneedle micromold can be prepared by a method including providing a mold substrate, FIG. 3A; coating the mold substrate with a protective layer, FIG. 3A; coating the protective layer with a photoresist layer, FIG. 3B; patterning the photoresist layer to form a first micro-patterned mask, FIG. 3C; etching the protective layer using the first micro-patterned mask to form a second micro-patterned mask, FIG. 3D; etching the substrate using the second micro-patterned mask to remove a portion of the substrate such that the second micro-patterned mask is gradually undercut to form from the substrate a positive microneedle micromold comprising one or more microneedles including a base end which tapers to a penetrating tip, wherein the penetrating tip contacts the second micro-patterned mask, FIG. 3E; and removing the second micro-patterned mask to release the positive microneedle micromold, FIG. 3F. A positive mold can be made of Si through isotropic etching. In alternative embodiments, a positive mold can be made of aluminum through high speed milling and chemical wet etching, for example, as shown in FIG. 7A and FIGS. 8A-8D.

In other embodiments, the microneedle mold can be formed by micromachining using additive or subtractive processes to create the microdepressions which define the shape of the microneedle. In one embodiment, the mold can be a negative mold made by a process comprising (a) microshaping a block of a first material to form a mold insert having a plurality of microprotrusions; and (b) depositing a second material onto the microprotrusions to form a micromold having a plurality of microdepressions defined by the microprotrusions.

Various methods known in the art can be used to fabricate various embodiments of the microneedles and/or microneedle devices of the invention. Other than molding as described earlier, isotropic etching can also be used to form silk fibroin into microneedles and/or microneedle device according to one or more embodiments of the invention. In other embodiments, reactive etching can be been applied to produce silk fibroin microneedles and/or microneedle device. In some embodiments, milling and etching (e.g., wet chemical etching) can be used to form silk fibroin into microneedles and/or microneedle device according to one or more embodiments of the invention.

In some embodiments, the microneedles or microneedle devices described herein can be sterilized. Sterilization methods for biomedical devices are well known in the art, including, but not limited to, gamma or ultraviolet radiation, autoclaving (e.g., heat/steam); alcohol sterilization (e.g., ethanol and methanol); and gas sterilization (e.g., ethylene oxide sterilization).

The methods provided herein can be used to generate silk fibroin-based microneedle tips of any dimensions ranging from about 50 nm to about 50 µm. In some embodiments, the silk fibroin-based microneedle tips can be constructed to have a diameter of 10 µm or less, including, e.g., but not limited to 2 µm or less, or even 100 nm or less. There is no fundamental limitation preventing the tips from having even smaller diameters (the limit of silk replica casting has been demonstrated with a resolution of tens of nm. Perry et al., 20 Adv. Mat. 3070 (2008)).

Further, the microneedles of the present invention can take advantage of the many techniques developed to functionalize silk fibroin (e.g., active agents such as dyes and sensors). See, e.g., U.S. Pat. No. 6,287,340, Bioengineered anterior cruciate ligament; WO 2004/000915, Silk Biomaterials & Methods of Use Thereof; WO 2004/001103, Silk Biomaterials & Methods of Use Thereof; WO 2004/062697, Silk Fibroin Materials & Use Thereof; WO 2005/000483, Method for Forming inorganic Coatings; WO 2005/012606, Concentrated Aqueous Silk Fibroin Solution & Use Thereof; WO 2011/005381, Vortex-Induced Silk fibroin Gelation for Encapsulation & Delivery; WO 2005/123114, Silk-Based Drug Delivery System; WO 2006/076711, Fibrous Protein Fusions & Uses Thereof in the Formation of Advanced Organic/Inorganic Composite Materials; U.S. Application Pub. No. 2007/0212730, Covalently immobilized protein gradients in three-dimensional porous scaffolds; WO 2006/042287, Method for Producing Biomaterial Scaffolds; WO 2007/016524, Method for Stepwise Deposition of Silk Fibroin Coatings; WO 2008/085904, Biodegradable Electronic Devices; WO 2008/118133, Silk Microspheres for Encapsulation & Controlled Release; WO 2008/108838, Microfluidic Devices & Methods for Fabricating Same; WO 2008/127404, Nanopatterned Biopolymer Device & Method of Manufacturing Same; WO 2008/118211, Biopolymer Photonic Crystals & Method of Manufacturing Same; WO 2008/127402, Biopolymer Sensor & Method of Manufacturing Same; WO 2008/127403, Biopolymer Optofluidic Device & Method of Manufacturing the Same; WO 2008/127401, Biopolymer Optical Wave Guide & Method of Manufacturing Same; WO 2008/140562, Biopolymer Sensor & Method of Manufacturing Same; WO 2008/127405, Microfluidic Device with Cylindrical Microchannel & Method for Fabricating Same; WO 2008/106485, Tissue-Engineered Silk Organs; WO 2008/140562, Electroactive Bioploymer Optical & Electro-Optical Devices & Method of Manufacturing Same; WO 2008/150861, Method for Silk Fibroin Gelation Using Sonication; WO 2007/103442, Biocompatible Scaffolds & Adipose-Derived Stem Cells; WO 2009/155397, Edible Holographic Silk Products; WO 2009/100280, 3-Dimensional Silk Hydroxyapatite Compositions; WO 2009/061823, Fabrication of Silk Fibroin Photonic Structures by Nanocontact Imprinting; WO 2009/126689, System & Method for Making Biomaterial Structures.

The silk fibroin-based microneedles can also be combined, even in monolithic fashion, with sensors that, for example, monitor the delivery of the active agent; or can include sensors for use in biological or other environments. See, e.g., WO 2010/126640, Nanoimprinting of Silk Fibroin Structures for Biomedical & Biophotonic Applications; WO 2008/127401; WO 2008/118211; WO 2008/127402; WO 2008/140562. The silk fibroin-based microneedles or microneedle devices of the present invention can also be combined with silk photonic structures, including holograms and silk optical fibers. See, e.g., WO 2009/061823; PCT/US10/50565, Drawn Silk E-Gel Fibers & Methods of Making Same; PCT/US2010/042585, All-Protein Implantable, Resorbable Reflectors; PCT/US10/47307, Silk Transistor Devices & Method of Making Transistor Devices from Silk.

In an alternative embodiment, the silk fibroin microneedles can include plasmonic nanoparticles that form, within the needles or base of a needle patch, a photothermal element. This approach takes advantage of the superior doping characteristics of silk fibroin. Thermal therapy has been shown to aid in the transdermal delivery of various agents, see Park et al., Effect of Heat on Skin Permeability, 359 Intl. J. Pharm. 94 (2008). In one embodiment, short bursts of heat on very limited areas can be used to maximize permeability with minimal harmful effects on surrounding tissues. Thus, plasmonic particle-doped microneedles can add specificity to thermal therapy not only by using tiny needles, but by focusing light to generate heat only via the needles themselves instead of surrounding tissues.

One embodiment of the present invention includes a microneedle device for transport of at least one active agent across or into a biological barrier. The microneedle device can include a silk fibroin substrate, and a plurality of silk fibroin microneedles integral with or attached to and extending from the substrate, wherein the silk fibroin microneedle comprises at least one active agent. An active agent can be contained in or on the substrate and/or the microneedles of the device. Thus, for example, a microneedle device in the form of a patch can be used to deliver agent in sustained release fashion as the agent diffuses through the substrate to the microneedles and from the microneedles to the tissue in contact with the microneedles.

Exemplary Applications of Microneedles or Microneedle Devices Described Herein

A further aspect provided herein relates to methods for delivering an active agent across a biological barrier. Such method includes providing at least one microneedle or at least one microneedle device described herein, wherein the microneedle or the microneedle device comprises at least one active agent; causing the microneedle or microneedle device to penetrate into the biological barrier; and allowing the active agent to be released from the microneedle. In some embodiments, the active agent is released into the biological barrier through degradation or dissolution of the microneedles.

In some embodiments, the microneedle or the microneedle device can be attached to an applicator to facilitate the administration of microneedles across or into a biological barrier. By way of example only, the microneedle(s) or the microneedle device(s) can be attached to, for example, a syringe or any injectors or microneedle administration devices described herein, for application. For internal tissues, application of the microneedles or microneedle device can be achieved with the aid of, for example, a catheter. In some embodiments, the microneedle(s) or microneedle device(s) can be surgically implanted.

The biological barrier can be any biological tissue of a subject in need of the active agent. Examples of biological barrier can include, but are not limited to, any cells, tissues, or organs, including the skin or parts thereof (e.g., stratum corneum, epidermis and dermal tissues), mucosal tissues, vascular tissues, lymphatic vessels, ocular tissues (e.g., cornea, conjunctiva, sclera), and cell membranes. In some embodiments, a biological barrier is skin.

The term "subject" includes, but is not limited to, mammals, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs. The term does not denote a particular age or sex. Thus, adult and newborn subjects, as well as fetuses, whether male or female, are intended to be covered. In one embodiment, the subject is a mammal. In one embodiment, the subject is a human subject.

In some embodiments, the microneedles or microneedle devices described herein can contain no active agent and be used to create micropores in a biological barrier (e.g., to permeabilize skin). In such embodiments, after insertion of the microneedle(s) or administration of microneedle device(s), the microneedle(s) or microneedle device(s) can be removed, followed by administration of an active agent through the micropores, e.g., using a transdermal patch comprising the active agent.

In some embodiments, the microneedle or microneedle devices can be adapted for use in transdermal delivery of an active agent. By way of example only, the microneedles or microneedle device described herein can be part of a transdermal patch. In such embodiments, further comprise an adhesive, and optionally a reservoir, e.g., in communication with the microneedles. The reservoir can contain an active agent for delivery through the microneedles. A wide variety of pharmaceuticals are now available in transdermal patch form, including, but not limited to, nicotine patch for helping cessation of tobacco smoking; opioid medications such as Fentanyl (marketed as Duragesic) and Buprenorphine (marketed as BuTrans) for pain relief; estrogen patches, e.g., for treating menopausal symptoms as well as post-menopausal osteoporosis; contraceptive patch (marketed as Ortho Evra or Evra) and testosterone patches for both men (Androde) and women (Intrinsa), e.g., to deliver hormones; nitroglycerin patches, e.g., for treatment of angina; scopolamine patch for treatment of motion sickness; anti-hypertensive drug Clonidine (Catapres-TTS); antidepressant patch such as Emsam, a transdermal form of the MAOI selegiline; Daytrana, a transdermal delivery agent for the Attention Deficit Hyperactivity Disorder (ADHD) drug methylphenidate (otherwise known as Ritalin or Concerta); Vitamin B12 (e.g., Cyanocobalamin, a highly stable form of vitamin B12); Rivastigmine, an Alzheimer's treatment medication, in patch form under the brand name Exelon; an insulin patch, and an antibiotic patch.

In some embodiments, the microneedle or microneedle devices can be adapted for use in transdermal delivery of growth hormones, e.g., but not limited to, the ones described herein.

In some embodiments, the microneedle or microneedle devices can be adapted for use in transdermal delivery of pain medications, e.g., but not limited to, the ones described herein.

In some embodiments, the microneedle or microneedle devices can be adapted for use in transdermal delivery of vaccine or vaccine products, e.g., but not limited to, the ones described herein.

In some embodiments where the microneedles or microneedle devices comprise at least one active agent, the rate of the active agent released from the microneedles can vary depending on, e.g., the properties and/or designs of the microneedles, and/or distribution of the active agents within the microneedles described herein. In some embodiments, the microneedles or microneedle devices can be characterized by one release profile of active agents into a biological barrier. In some embodiments, the microneedles or microneedle devices can be characterized by two or more release profiles of active agents into a biological barrier. For example, microneedles containing a fluidic channel therein can provide a rapid release of active agent when an active agent is administered through the fluidic channel to a biological barrier. Meanwhile, active agents can also be released from the bulk of the microneedles at a relatively slower rate into a biological barrier through degradation or dissolution of the microneedles.

In some embodiments, a desired amount of at least one active agent can be released from the microneedle described herein over a pre-defined period of time. In some embodiments, at least about 5% of an active agent, including at least about 10%, at least about 15%, at least about 20%, at least about 30%, at least about 40%, at least about 50%, at least about 60%, at least about 70%, at least about 80%, at least about 90%, at least about 95%, or at least about 97%, about 98%, or about 99% of the active agent, or 100% of the active agent, can be released from the microneedle over a pre-defined period of time. In such embodiments, the desired amount of the active agent can be released from the microneedle over seconds, minutes, hours, months or years. In some embodiments, the desired amount of the active agent can be released from the microneedle instantaneously upon insertion into a tissue, e.g., within 5 seconds, within 10 seconds, within 30 seconds, 1 minute or longer. In some embodiments, the desired amount of the active agent can be released from the microneedle over a period of at least about 1 hour, at least about 2 hours, at least about 3 hours, at least about 6 hours, at least about 12 hours, at least about 1 day, at least about 2 days, at least about 3 days, at least about 4 days, at least about 5 days, at least about 6 days, at least about 1 week, at least about 2 weeks, at least about 1 month, at least about 2 months, at least about 3 months, at least about 6 months or longer. In some embodiments, the desired amount of the active agent can be released from the microneedle over about 1 year, about 2 years, about 3 years, about 4 years or longer.

In some embodiments, the release of active agents from the microneedles and/or microneedle devices described can be controlled by the dissolution rate and/or solubility of the silk fibroin-based microneedles. In such embodiments, at least about 5% of silk fibroin-based microneedles, including at least about 10%, at least about 15%, at least about 20%, at least about 30%, at least about 40%, at least about 50%, at least about 60%, at least about 70%, at least about 80%, at least about 90%, at least about 95%, or at least about 97%, about 98%, or about 99% of the active agent, or 100% of the silk fibroin-based microneedles, can dissolve or degrade over a pre-defined period of time. In such embodiments, the degradation or dissolution can occur over seconds, minutes, hours, months or years. In some embodiments, the degradation or dissolution of the microneedles can occur instantaneously upon insertion into a tissue, e.g., within 5 seconds, within 10 seconds, within 30 seconds, 1 minute or longer. In some embodiments, the dissolution or degradation can occur over a period of at least about 1 hour, at least about 2 hours, at least about 3 hours, at least about 6 hours, at least about 12 hours, at least about 1 day, at least about 2 days, at least about 3 days, at least about 4 days, at least about 5 days, at least about 6 days, at least about 1 week, at least about 2 weeks, at least about 1 month, at least about 2 months, at least about 3 months, at least about 6 months or longer. In some embodiments, the dissolution or degradation can occur over about 1 year, about 2 years, about 3 years, about 4 years or longer. Methods to determine appropriate release rate of active agents into a biological barrier is well known in the art, e.g., using the methods described in the Examples.

In another aspect, the microneedle or microneedle device can be used for extracting biological molecules (e.g. biomarker molecules) from a biological barrier. For example, the microneedles can be coated with, for example, but not limited to, peptides, proteins, antibodies, biomarker-binding molecules and/or ligand-binding molecules, and then inserted into a biological barrier of a subject. The biological molecules or biomarker molecules that are bound on the microneedle surface can then be analyzed, e.g., for diagnostic purposes.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not. Additionally, the term "comprising" or "comprises" includes "consisting essentially of" and "consisting of."

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the phrases "silk fibroin-based microneedles" and "silk fibroin microneedles" generally refer to microneedles comprising silk fibroin. In some embodiments, the phrase "silk fibroin-based microneedles" refers to each microneedle in which silk fibroin constitutes at least about 30% of the total composition, including at least about 40%, at least about 50%, at least about 60%, at least about 70%, at least about 80%, at least about 90%, at least about 95% or higher, of the total composition. In certain embodiments, the silk fibroin-based microneedles can be substantially formed from silk fibroin. In various embodiments, the silk fibroin-based microneedles can be substantially formed from silk fibroin comprising at least one active agent.

As used herein, the term "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

The term "stabilize," and "stabilization," are used herein in reference to maintaining or retaining bioactivity of at least one active agent in silk fibroin-based microneedles. The phrase "stabilization of active agents" as used herein means that one or more active agents distributed, dispersed or embedded in silk fibroin-based microneedles retain at least about 30% of its original bioactivity, including at least about 40%, at least about 50%, at least about 60%, at least about 70%, at least about 80%, at least about 90% of its original bioactivity or higher. The terms "stabilize" and "retain" in reference to bioactivity of active agents are used herein interchangeably.

As used herein, the terms "maintaining," and "maintain," when referring to the microneedles comprising active agents mean keeping, sustaining, or retaining the bioactivity of at least one active agent in silk fibroin-based microneedles described herein, when the active agent is subjected to certain conditions. In some embodiments, one or more active agents distributed in a silk fibroin-based microneedles retains at least about 30% of its original bioactivity, including at least about 40%, at least about 50%, at least about 60%, at least about 70%, at least about 80%, at least about 90% of its original bioactivity or higher.

The term "bioactivity," as used herein in reference to an active agent, generally refers to the ability of an active agent to interact with a biological target and/or to produce an effect on a biological target. For example, bioactivity can include, without limitation, elicitation of a stimulatory, inhibitory, regulatory, toxic or lethal response in a biological target. The biological target can be a molecule or a cell. For example, a bioactivity can refer to the ability of an active agent to modulate the effect/activity of an enzyme, block a receptor, stimulate a receptor, modulate the expression level of one or more genes, modulate cell proliferation, modulate cell division, modulate cell morphology, or any combination thereof. In some instances, a bioactivity can refer to the ability of a compound to produce a toxic effect in a cell.

The bioactivity can be determined by assaying a cellular response. Exemplary cellular responses include, but are not limited to, lysis, apoptosis, growth inhibition, and growth promotion; production, secretion, and surface exposure of a protein or other molecule of interest by the cell; membrane surface molecule activation including receptor activation; transmembrane ion transports; transcriptional regulations; changes in viability of the cell; changes in cell morphology; changes in presence or expression of an internal component of the cell; changes in presence or expression of a nucleic acid produced within the cell; changes in the activity of an enzyme produced within the cell; and changes in the presence or expression of a receptor. Methods for assaying different cellular responses are well known to one of skill in the art, e.g., western blot for determining changes in presence or expression of an endogenous protein of the cell, or microscopy for monitoring the cell morphology in response to the active agent.

In reference to an antibody, the term "bioactivity" includes, but is not limited to, epitope or antigen binding affinity, the in vivo and/or in vitro stability of the antibody, the immunogenic properties of the antibody, e.g., when administered to a human subject, and/or the ability to neutralize or antagonize the bioactivity of a target molecule in vivo or in vitro. The aforementioned properties or characteristics can be observed or measured using art-recognized techniques including, but not limited to, scintillation proximity assays, ELISA, ORIGEN immunoassay (IGEN), fluorescence quenching, fluorescence ELISA, competitive ELISA, SPR analysis including, but not limited to, SPR analysis using a BIAcore biosenser, in vitro and in vivo neutralization assays (see, for example, International Publication No. WO 2006/062685), receptor binding, and immunohistochemistry with tissue sections from different sources including human, primate, or any other source as needed. In reference to an immunogenic substance, the "bioactivity" includes immunogenicity, the definition of which is discussed in detail later. In reference to a virus, the "bioactivity" includes infectivity, the definition of which is discussed in detail later. In reference to a contrast agent, e.g., a dye, the "bioactivity" refers to the ability of a contrast agent when administered to a subject to enhance the contrast of structures or fluids within the subject's body. The bioactivity of a contrast agent also includes, but is not limited to, its ability to interact with a biological environment and/or influence the response of another molecule under certain conditions.

By "original bioactivity" in reference to an active agent is generally meant the bioactivity of an active agent as measured immediately before or immediately after the active agent is introduced into silk fibroin-based microneedles. That is, the original bioactivity of an active agent can be measured, for example, within about 20 minutes, before or after the active agent is introduced into silk fibroin-based microneedles. In some instances, the original bioactivity of an active agent can be measured, for example, about 10 seconds, about 15 seconds, about 20 seconds, about 25 seconds, about 30 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes, before or after the active agent is introduced into silk fibroin-based microneedles. In another embodiment, the term "original bioactivity," as used herein, can be used to describe the bioactivity of an active agent before the active agent is introduced into silk fibroin-based microneedles. In some embodiments, the term "original bioactivity" refers to the maximum bioactivity of an active agent, e.g., bioactivity measured immediately after activation of the active agent, e.g., by reconstitution or by increasing the temperature. For example, if the active agent is initially in powder, the original bioactivity of the active agent can be measured immediately after reconstitution. In some embodiments, the term "original bioactivity" refers to bioactivity of an active agent dispersed in non-silk fibroin-based microneedles when stored or transported under conditions specified by the manufacturer. In some embodiments, the term "original bioactivity" refers to bioactivity of an active agent when stored or transported in silk fibroin-based microneedles as described herein under conditions specified by the manufacturer.

The term "immunogenicity" refers to the ability of a substance, such as an antigen or epitope, to provoke humoral and/or cell-mediated immunological response in a subject. A skilled artisan can readily measure immunogenicity of a substance. The presence of a cell-mediated immunological response can be determined by any art-recognized methods, e.g., proliferation assays (CD4+ T cells), CTL (cytotoxic T lymphocyte) assays (see Burke, supra; Tigges, supra), or immunohistochemistry with tissue section of a subject to determine the presence of activated cells such as monocytes and macrophages after the administration of an immunogen. One of skill in the art can readily determine the presence of humoral-mediated immunological response in a subject by any well-established methods. For example, the level of antibodies produced in a biological sample such as blood can be measured by western blot, ELISA or other methods known for antibody detection.

As used herein, the term "infectivity" in reference to a virus means the characteristic of a virus that embodies capability of entering, surviving in, and multiplying or causing an immunological response in a susceptible host. Any methods known to a skilled artisan for determination of virus infectivity can be used for the purposes described herein.

The present invention can be defined in any of the following numbered paragraphs:
1. A microneedle comprising silk fibroin, wherein said microneedle has a base and a penetrating tip, the tip having a dimension ranging from about 50 nm to about 50 µm.
2. The microneedle of paragraph 1, wherein the dimension of the tip ranges from about 200 nm to about 40 µm.
3. The microneedle of paragraph 1 or 2, further comprising at least one active agent.

4. The microneedle of paragraph 3, wherein the active agent is selected from the group consisting of proteins, peptides, antigens, immunogens, vaccines, antibodies or portions thereof, antibody-like molecules, enzymes, nucleic acids, siRNA, shRNA, aptamers, viruses, bacteria, small molecules, cells, hormones, antibiotics, therapeutic agents, diagnostic agents, and any combinations thereof.
5. The microneedle of any of paragraphs 1-4, wherein the active agent is antibiotics.
6. The microneedle of any of paragraphs 1-5, wherein the active agent retains at least about 30% of its original bioactivity when the microneedle is maintained for at least about 24 hours at a temperature above 0° C.
7. The microneedle of any of paragraphs 1-6, wherein the active agent retains at least about 50% of its original bioactivity.
8. The microneedle of paragraph 6 or 7, wherein the microneedle is maintained for at least about 1 month.
9. The microneedle of any of paragraphs 6-8, wherein the microneedle is maintained at a temperature of about 0° C. to above room temperature.
10. The microneedle of any of paragraphs 6-9, wherein the microneedle is maintained at a temperature of about room temperature to about 37° C.
11. The microneedle of any of paragraphs 1-10, further comprising one or more biodegradable polymers.
12. The microneedle of any of paragraphs 1-11, wherein the microneedle degrades at a controlled rate upon contact with a biological environment.
13. The microneedle of paragraph 12, wherein the degradation of the microneedle controls release of the active agents distributed therein.
14. A microneedle device, comprising:
   a substrate and one or more silk fibroin microneedles integrated or attached to the substrate and extending from the substrate,
   wherein each microneedle comprises a base and a penetrating tip.
15. The device of paragraph 14, wherein the microneedle further comprises at least one active agent.
16. The device of paragraph 15, wherein the active agent is selected from the group consisting of proteins, peptides, antigens, immunogens, vaccines, antibodies or portions thereof, antibody-like molecules, enzymes, nucleic acids, siRNA, shRNA, aptamers, viruses, bacteria, small molecules, cells, hormones, antibiotics, therapeutic agents, diagnostic agents, and any combinations thereof.
17. The device of any of paragraphs 14-16, wherein the active agent retains at least about 30% of its original bioactivity when the device is maintained for at least about 24 hours at a temperature above 0° C.
18. The device of any of paragraphs 14-17, wherein the active agent retains at least about 50% of its original bioactivity.
19. The device of paragraph 17 or 18, wherein the device is maintained for at least about 1 month.
20. The device of any of paragraphs 17-19, wherein the device is maintained at a temperature of about 0° C. to above room temperature.
21. The device of any of paragraphs 17-20, wherein the device is maintained at a temperature of about room temperature to about 37° C.
22. The device of any of paragraphs 14-21, wherein the silk fibroin microneedle ranges from about 15 μm to about 1500 μm in length.
23. The device of paragraph 22, wherein the silk fibroin microneedle ranges from about 150 μm to about 1000 μm in length.
24. The device of any of paragraphs 14-23, wherein the length of at least one of the silk fibroin microneedles is different from the others.
25. The device of any of paragraphs 14-24, wherein silk fibroin microneedle further comprises one or more biodegradable polymers.
26. The device of any of paragraphs 14-25, wherein the silk fibroin microneedle degrades at a controlled rate upon contact with a biological environment.
27. The device of any of paragraphs 14-26, wherein the substrate comprises one or more biocompatible polymer.
28. The device of any of paragraphs 14-27, wherein the substrate conforms to a surface upon contact with the surface.
29. The device of any of paragraphs 14-28, wherein the substrate comprises silk fibroin and integrated with the silk fibroin microneedles.
30. A microneedle for storing and delivering an active agent, comprising at least one active agent and silk fibroin, wherein said microneedle has a base and a penetrating tip, the tip having a dimension ranging from about 50 nm to about 50 μm, and wherein the active agent retains at least about 30% of its original bioactivity when the microneedle is maintained for at least about 24 hours at a temperature above 0° C.
31. The microneedle of paragraph 30, wherein the dimension of the tip ranges from about 200 nm to about 40 μm.
32. The microneedle of any of paragraphs 30-31, wherein the active agent retains at least about 50% of its original bioactivity.
33. The microneedle of any of paragraphs 30-32, wherein the microneedle is maintained for at least about 1 month.
34. The microneedle of any of paragraphs 30-33, wherein the microneedle is maintained at a temperature of about 0° C. to above room temperature.
35. The microneedle of paragraph 34, wherein the microneedle is maintained at a temperature of about room temperature to about 37° C.
36. The microneedle of any of paragraphs 30-35, wherein the active agent is released into a biological barrier via controllable degradation of the microneedle.
37. A method of delivering an active agent to across or into a biological barrier, comprising:
   providing a microneedle comprising silk fibroin and the active agent;
   causing the microneedle to penetrate into the biological barrier, and
   allowing the active agent to be released from the microneedle.
38. The method of paragraph 37, wherein the biological barrier is a tissue of a subject.
39. The method of paragraph 38, wherein the tissue is skin.
40. The method of any of paragraphs 37-39, wherein the active agent is released through degradation of the microneedle in the tissue of the subject.
41. A method of fabricating a silk fibroin-based microneedle device comprising one or more silk fibroin microneedles, the method comprising:
   providing a microneedle micromold comprising a micromold substrate and one or more holes in the micromold substrate, wherein the interior surface of the hole in the micromold substrate defines an exterior surface of the microneedle;

filling the microneedle micromold with a silk fibroin solution;

drying the silk fibroin solution to form a silk-based microneedle with an exterior surface defined by the interior surface of the hole of the microneedle micromold; and separating the silk-based microneedle device from the microneedle micromold.

42. The method of paragraph 41, further comprising blending the silk fibroin solution with at least one active agent prior to the drying step.

43. The method of paragraph 41 or 42, further comprising coating at least one silk fibroin microneedle with at least one layer of an active agent.

44. The method of any of paragraphs 41-43, further comprising blending the silk fibroin solution with at least one biodegradable polymer prior to the drying step.

45. The method of any of paragraphs 41-44, wherein the microneedle micromold is overfilled with a silk fibroin solution so that a layer of silk fibroin solution is formed over the microneedle micromold and subsequently dried into a substrate which is attached to the microneedles and supports the microneedles.

46. The method of paragraph 45, wherein the silk fibroin substrate is conformable to a surface upon contact with the surface.

47. The method of any of paragraphs 41-46, further comprising, prior to the separating step:

depositing a biopolymer solution over the dried silk-based microneedle device; and drying the biopolymer solution thereby forming a substrate attaching to the microneedles and supporting the microneedles.

48. The method of paragraph 47, wherein the biopolymer substrate is conformable to a surface upon contact with the surface.

49. The method of any of paragraphs 41-48, further comprising the step of modulating the solubility of the silk fibroin microneedles.

50. The method of paragraph 49, wherein the modulating step comprises water annealing or methanol treatment to increase the time duration for dissolution of the silk fibroin microneedles.

51. The method of any of paragraphs 41-50, further comprising generating a porous structure in the silk fibroin microneedle.

52. The method of any of paragraphs 41-51, wherein the microneedle micromold is prepared by steps comprising:

providing a mold substrate;

coating the mold substrate with a protective layer;

coating the protective layer with a photoresist layer;

patterning the photoresist layer to form a first micro-patterned mask;

etching the protective layer using the first micro-patterned mask to form a second micro-patterned mask;

etching the mold substrate using the second micro-patterned mask to remove a portion of the mold substrate such that the second micro-patterned mask is gradually undercut to form from the mold substrate a positive microneedle micromold comprising one or more microneedles including a base end which tapers to a penetrating tip, wherein the penetrating tip contacts the second micro-patterned mask; and removing the second micro-patterned mask to release the positive microneedle micromold.

53. The method of paragraph 52, wherein the etching includes one or more of anisotropically etching, isotropic dry etching, or isotropic wet etching.

54. The method of any of paragraphs 52-53, wherein the material subjected to isotropic etching to form the positive microneedle mold is glass, metal, semiconductor, polymer, ceramic, or a hybrid material of any of these.

55. The method of any of paragraphs 52-54, wherein the material of the protective layer comprises $Si_3N4$, oxides, nitrides, metals, polymers, semiconductors, or other organic materials.

56. The method of any of paragraphs 52-55, wherein the step of patterning the photoresist layer comprises photolithography.

57. The method of any of paragraphs 52-56, wherein etching controls the geometry of the microneedle.

58. The method of any of paragraphs 54-57, wherein etching produces positive microneedle micromold having a penetrating tip with a diameter no more than 1 μm.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

An Exemplary Method of Microneedle Fabrication Using a Silicone Microneedle Molding Master A scheme for the fabrication of an embodiment of the invention comprising silk fibroin microneedles is shown in FIGS. 3A-3K. (FIG. 3A) The substrate used for fabrication is a silicone (Si) wafer with a 200 nm thick low stress silicone nitride ($Si_3N_4$) layer; (FIG. 3B) The wafer is coated with 1 μm positive tone photoresist (S1813, Rohm & Haas); (FIG. 3C) Photolithography is performed, leaving circular photoresist patterns functioning as a mask for the subsequent etching step; (FIG. 3D) Anisotropic reactive ion etching (RIE) is performed with $SF_6$ gas to etch the patterned $Si_3N_4$ film and expose the underlying Si material; (FIG. 3E) A timed isotropic wet etch is performed with a mixture of hydrofluoric-, nitric- and acetic acid (HNA) to undercut the $Si_3N_4$ mask; (FIG. 3F) A brief ultrasonic bath removes the residual $Si_3N_4$ circular mask and exposes the underlying Si microneedle molds; (FIG. 3G) Polydimethylsiloxane (PDMS) polymer is poured over the positive Si microneedle molds and cured; (FIG. 3H) The negative PDMS mold is removed from the Si master; (FIG. 3I) Aqueous silk fibroin solution is blend with the desired drug; (FIG. 3J) Drug loaded silk solution is poured over the PDMS mold and the solution is allowed to dry to form a film; and (FIG. 3K) The microneedle patterned and drug loaded silk film is removed from the master.

Figure 4A:
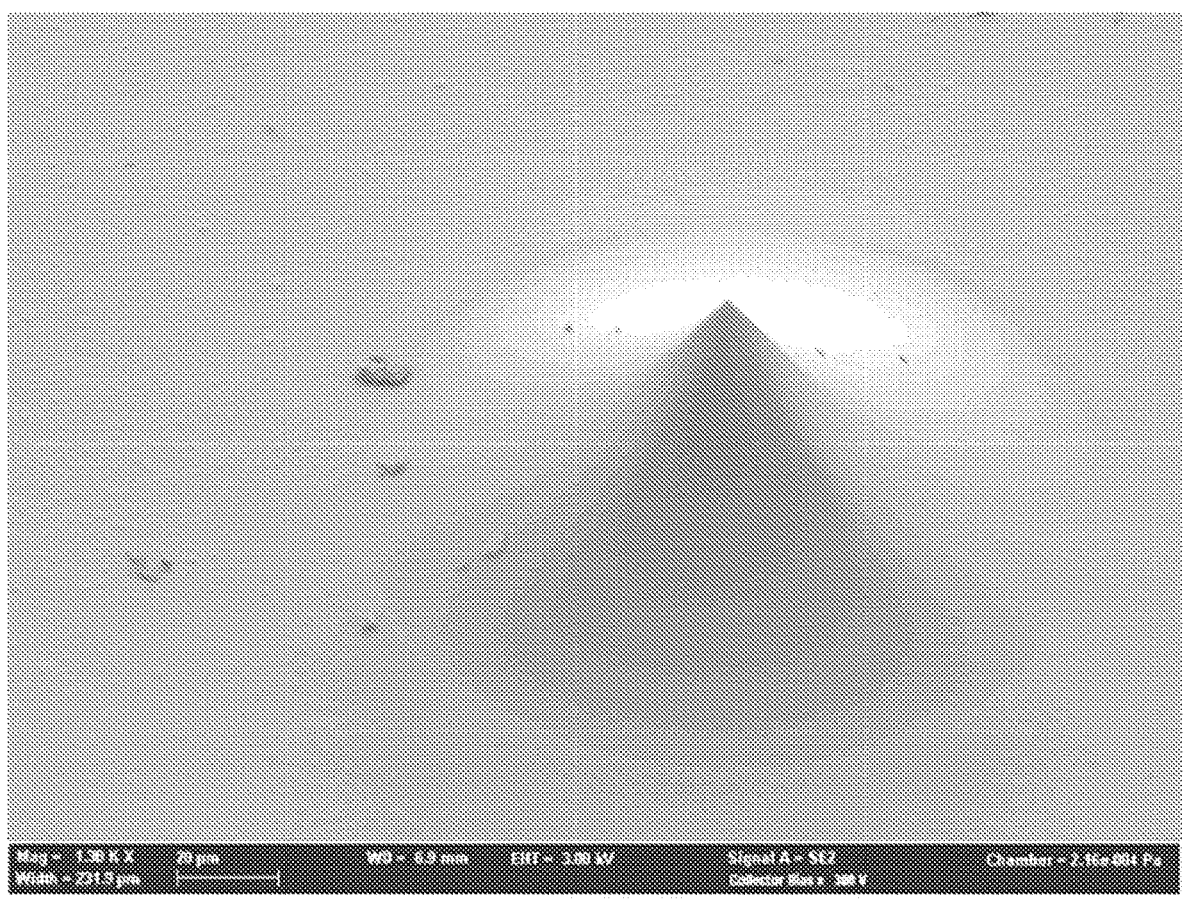
FIGS. 4A-4C show photographs of an exemplary microneedle positive molding master and resultant microneedles in accordance with one embodiment of the invention.
Figure 4B:
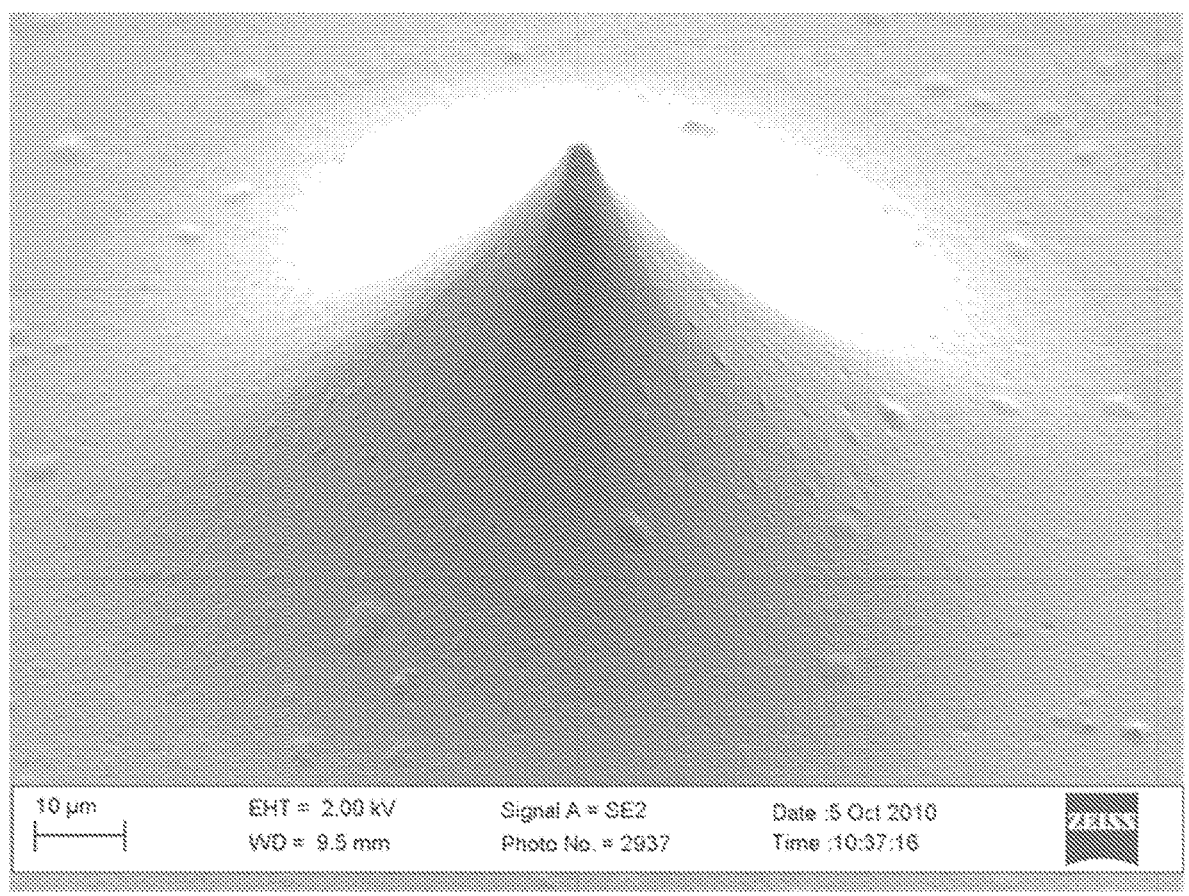
Figure 4C:
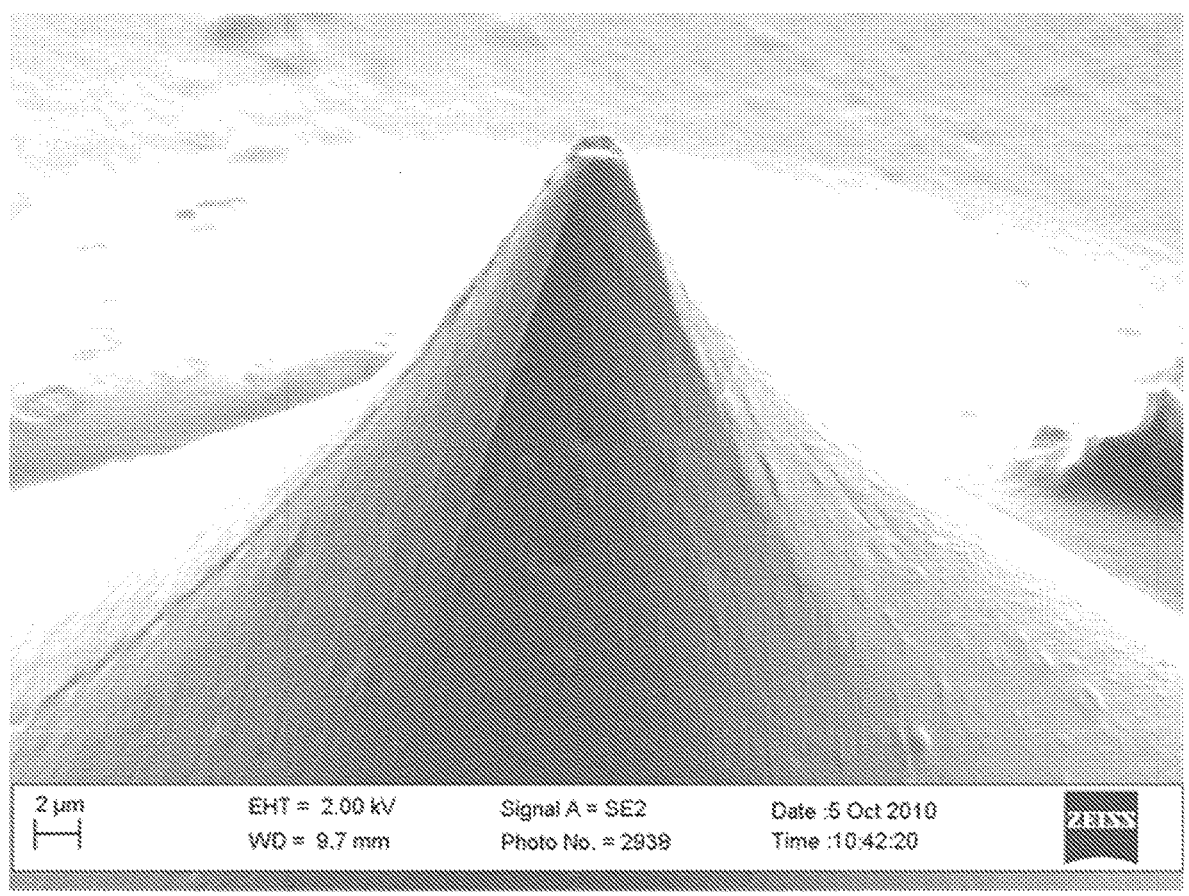
Figure 5:
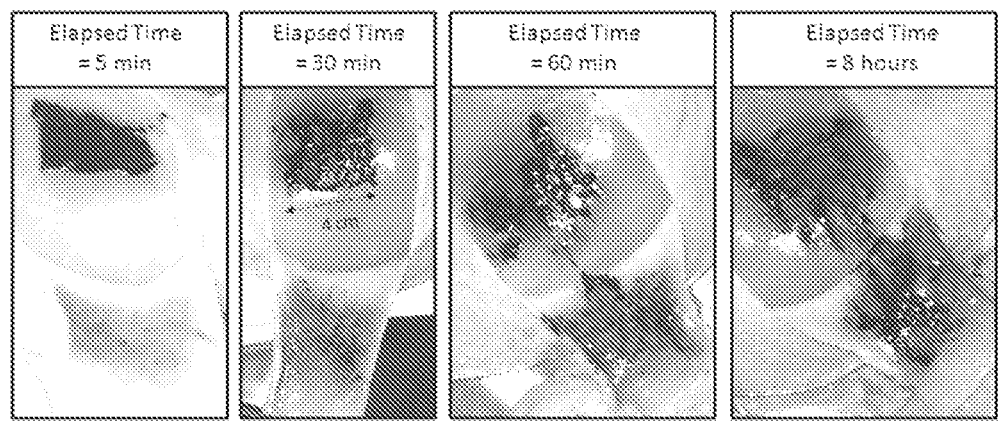
FIG. 5 compares the release of indigo dye from methanol-treated silk fibroin films with untreated films. Untreated films (top) dissolve partially to release the indigo dye when brought into contact with tissue; while methanol-treated films (bottom) release the indigo dye via diffusion.
Figure 5:
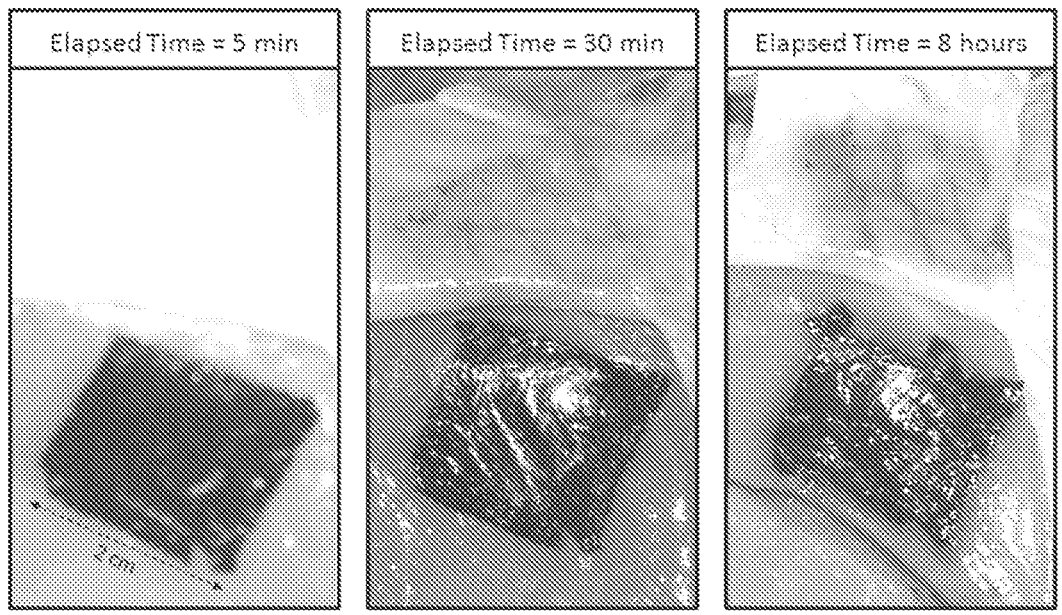
Figure 6A:
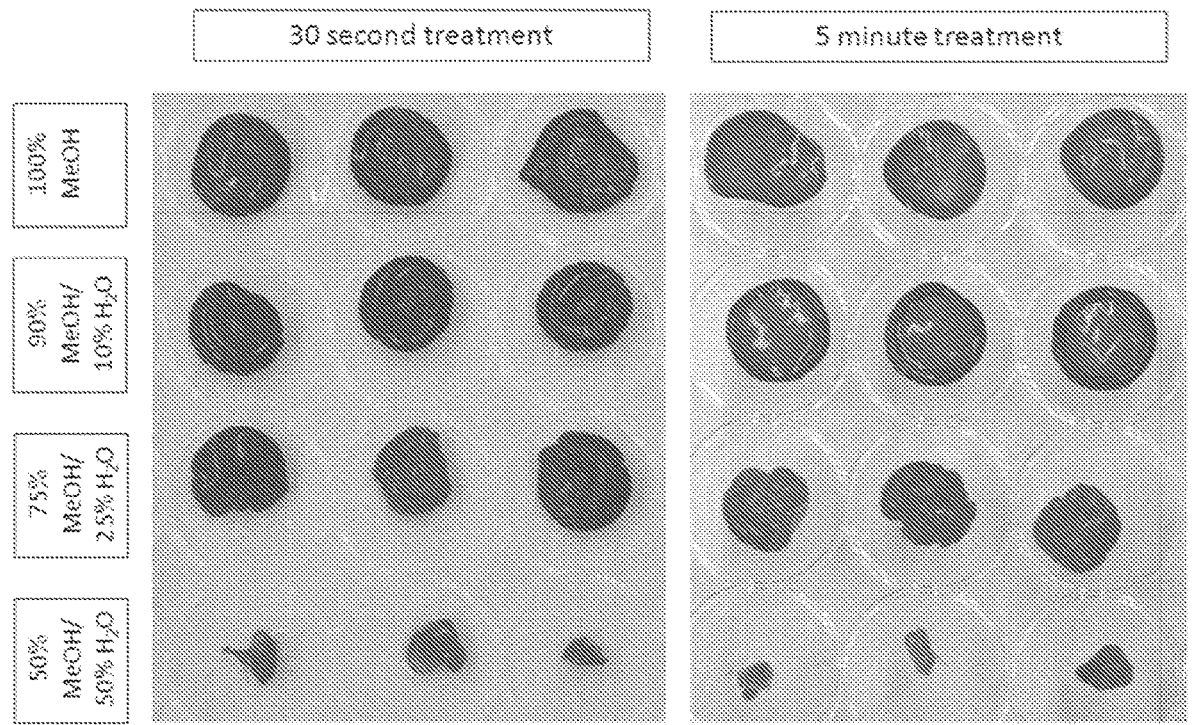
FIGS. 6A-6C show the effect of methanol treatment on swelling and drug release behaviors of silk fibroin films.
Figure 6B:
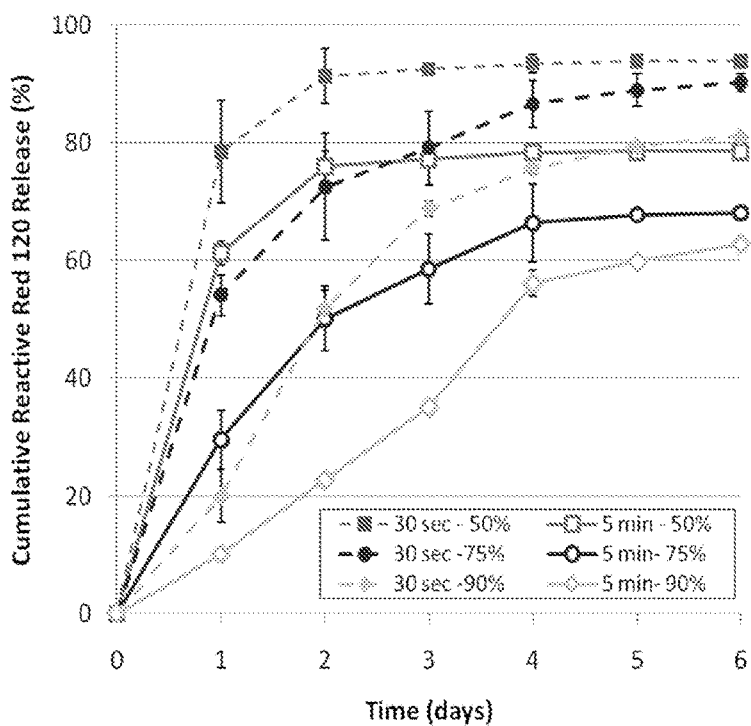
Figure 6C:
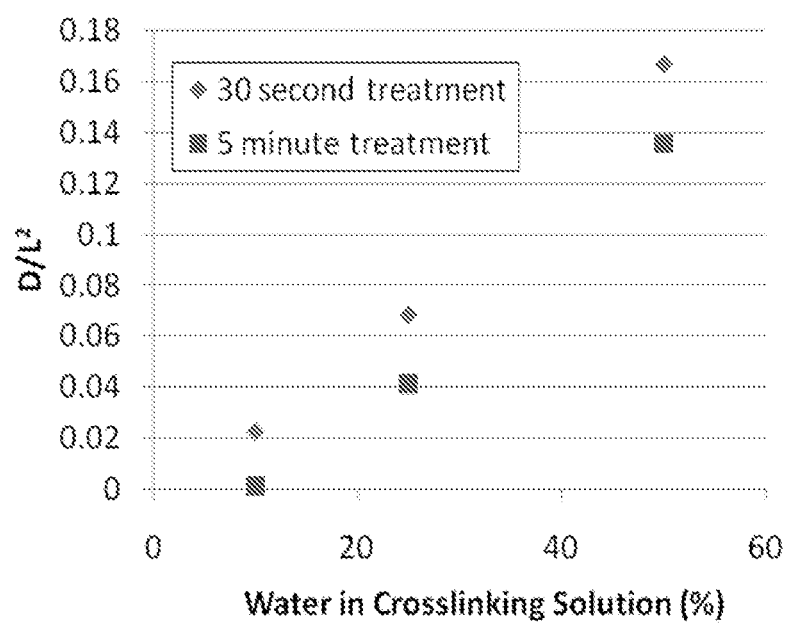
Figure 7A:
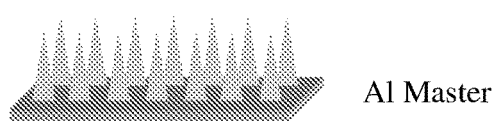
FIGS. 7A-7F show exemplary steps of a schematic process for fabricating one or more embodiments of the invention comprising silk fibroin microneedles.
Figure 7B:
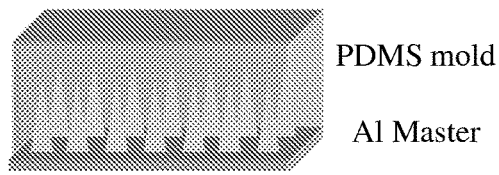
Figure 7C:
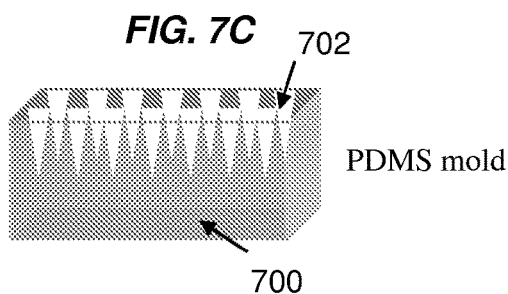
Figure 7D:
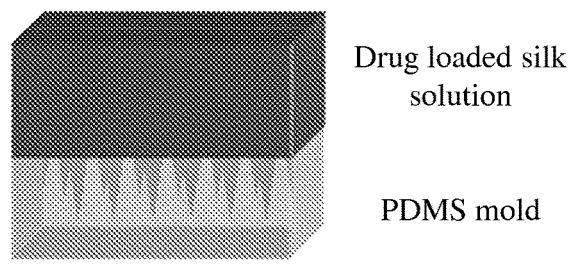
Figure 7E:
Figure 7F:

The structures of the resulting microneedles were analyzed by magnification. FIG. 4A shows a Si microneedle molding master, bottom diameter 150 μm, height 60 μm and tip radius <500 nm. FIG. 4B shows a Silk fibroin microneedle structure according to one embodiment of the invention, replicating the original Si master with high accuracy. FIG. 4C shows a magnified view of the silk microneedle tip, measuring less than 2 μm in diameter. In contrast to previous polymer based dissolvable microneedle designs (Sullivan et al., 16 Nature Med. 915 (2010)), the present fabrication method resulted in sharper tips (<2 μm vs. >10 μm), thus increasing the probability of each needle penetrating the skin and therefore increasing the overall amount of agent administered to the subject.

Example 2

Figure 9A:
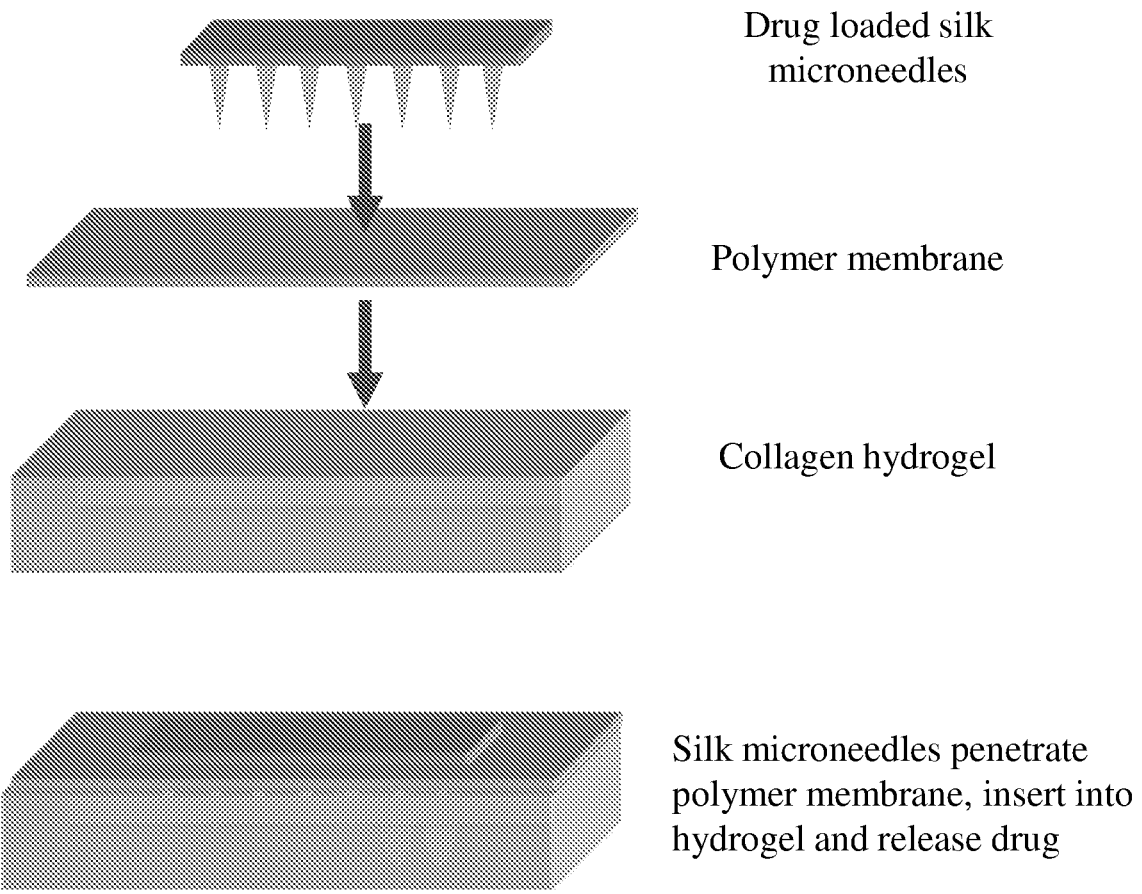
FIGS. 9A-9C show an exemplary study model and results of molecule release, e.g., drugs, from the silk fibroin microneedles according to one or more embodiments of the invention.

Drug Loading, Silk Processing, and Drug Release Kinetics of Silk Film

FIG. 5 shows that agent release from silk fibroin-based films can be controlled via thickness, β-sheet content, and molecular weight. In one embodiment, increasing film thickness, increasing β-sheet content and increasing degumming time (corresponding to decreasing average molecular weight) all increase release duration and decrease average release rate. Thin, methanol-crosslinked silk films containing 0.25 mg of GFP per film, released 92.8%±7% of their total drug load within 24 hours, but this release rate could be altered easily to control the release behavior to the target application. FIG. 5 shows that methanol-treated silk films loaded with indigo dye exhibited slower release into chicken breast tissue than untreated films. As shown in FIG. 5, the untreated films (top) dissolved partially when brought into contact with tissue, while methanol-treated films (bottom) relied solely on diffusion.

Methanol treatment, both concentration and duration of treatment, affect swelling and agent release from silk fibroin materials. FIG. 6A shows photographs of hydrated silk fibroin films loaded with reactive red-120 (a model dye, MW=~1500; Sigma-Aldrich, St. Louis, Mo.), reflecting the cumulative release behavior of the various films, and $D/L^2$ (a measure of film permeability), comparing different concentrations of methanol, with methanol treatment for 30 sec, with methanol treatment for 5 min. The data are also depicted graphically in FIGS. 6B and 6C, and show that the tertiary structures of silk fibroin can be manipulated to control the release rate of a given agent. It should be noted that as an alternative to methanol, ethanol can be used on silk fibroin microneedles to affect silk fibroin structure and agent release profiles.

Example 3

Another Exemplary Method of Microneedle Fabrication Using an Aluminum Microneedle Molding Master FIGS. 7A-7F illustrates a schematic diagram of an exemplary process to fabricate silk microneedles according to one or more embodiments of the invention. The effectiveness of such technique is demonstrated by micromolding of silk fibroin microneedles at ambient pressure and temperature. The aqueous-derived silk fibroin microneedles can generally reproduce the Al molding master. In some embodiments, the aqueous-derived silk fibroin microneedles can be approximately 500 micrometers high, with tip radii of <10 micrometers. In some embodiments, the silk fibroin microneedles can be doped with at least one active agent. As shown in later Examples, some embodiments of the silk fibroin microneedles can be doped with the horseradish peroxidase (HRP) enzyme as a large molecule model drug. In other embodiments, the silk fibroin microneedles can be loaded with an antibiotic tetracycline. For the purposes of visualization, in some embodiments, reactive red 120 dye was incorporated into the silk fibroin microneedles as depicted in FIGS. 8E-8F.

The aluminum (Al) microneedle molding masters were fabricated in a high speed micromilling approach followed by isotropic wet etching (FIGS. 7A and 8A). The milling step provides microneedle templates with dimension that approximate the desired topology (FIG. 8A) while the timed chemical etching of the Al templates refines the structure (FIGS. 8B and 8D), yielding a needle array of approximately 500 micrometers needle height and tip radii of <10 micrometers (FIG. 8C). These Al microneedle masters were used to fabricate an elastomer-based microneedle negative mold using a soft elastomer material, e.g., polydimethylsiloxane (PDMS) by using well-established soft-lithography techniques [25] (FIGS. 7B-7C). Employing this soft elastomer material can provide reproducible micron-scale features and ease of detaching the silk fibroin structures from the soft elastomer material, thus minimizing the probability of damaging the resulting devices [19]. Furthermore, the surface properties of PDMS can be modified from hydrophobic to partially hydrophilic, for example, by briefly exposing the elastomer surface to oxygen plasma [26] or any other methods known in the art. In addition, the porous network of PDMS can allow removal of water through the elastomer [27]. These are some examples of the essential characteristics to obtain high aspect-ratio silk structures in the molding process.

Aqueous silk fibroin solution (6%-8% wt/vol) was cast over the PDMS template (FIG. 7D). In some embodiments, the aqueous silk fibroin solution can further comprise at least one drug. In some embodiments, the PDMS template can be treated, e.g., by briefly exposing the PDMS surface to oxygen plasma. After the silk fibroin solution transitions to a solid-state (FIG. 7E), e.g., by overnight drying [28], an array of the silk fibroin microneedles can then be detached from the PDMS mold (FIGS. 7F, 8E-8F). The resulting silk fibroin microneedles can be further modified by post-processing, e.g., to adjust the degradation rate of the silk fibroin microneedles and/or diffusion properties of active agents embedded therein. This degree of control can be achieved, for example, by adjusting the protein secondary structure. Without wishing to be bound by theory, high content of beta sheet secondary structure can render the silk fibroin films water-insoluble. The beta sheet content can be controlled by various methods, including, but not limited to, adjusting the hydration state of the silk material [28] through its drying rate [29], exposure to methanol or high humidity (e.g. water vapor annealing), or various temperature, mechanical and electrical exposures [28-31]. Adjusting the amount of beta sheet content can yield silk fibroin materials with controlled crystallinity, solubility and release kinetics [30-33]. In some embodiments, various water vapor annealing times can be used to adjust the drug release properties of the silk fibroin needles. These post-processing steps can allow control over the diffusivity of the silk microneedles, ultimately providing control over drug release kinetics.

Example 4

Determination of Silk Fibroin Microneedle Release Kinetics

To demonstrate control over silk fibroin microneedle release kinetics, a gelatin or collagen hydrogel and polymer film membrane construct was used (FIGS. 9A-9C). A 10-20% gelatin hydrogel or collagen hydrogel was selected due to its common use as a tissue analog in ballistic testing [34]. In addition, collagen hydrogels are optically transparent, thus allowing assessment of the release kinetics. Furthermore, the water content, diffusion and mechanical properties of the collagen hydrogels can also be adjusted. The polymer membrane has a dual purpose: (1) simulating the outer layer of the skin to demonstrate successful piercing of the membrane for adequate mechanical toughness of the needles; and (2) functioning as a diffusion barrier to prevent the bulk silk fibroin substrate of the silk fibroin microneedle array from releasing the model drug into the underlying collagen hydrogel (i.e. to ensure that the monitored release is from the needles alone) [35, 36]. The polymer membrane was first placed over the HRP-loaded microneedles patch followed by application to the collagen hydrogel slab as shown in FIG. 9A. In some embodiments, mammal skin, e.g., porcine skin, can be used as a model to assess silk fibroin microneedle release kinetics, and/or mechanical property (e.g., penetrating capability) of the microneedles described herein.

Figure 9B:
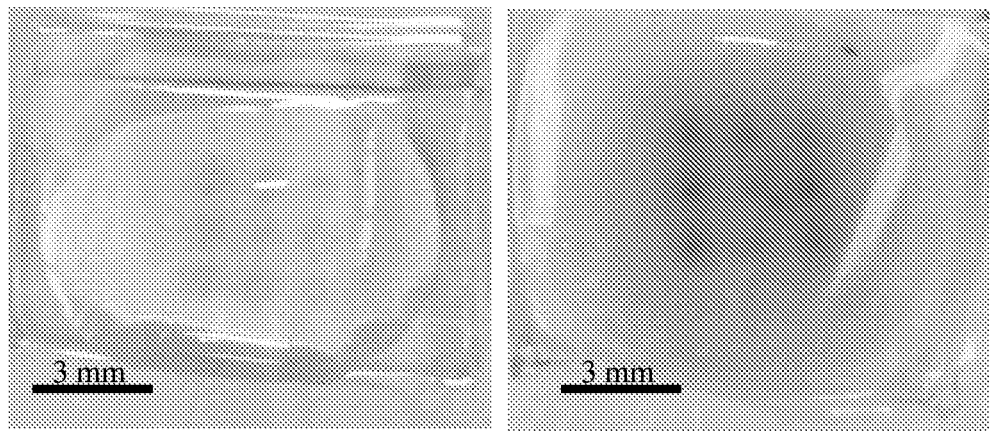
Figure 9C:
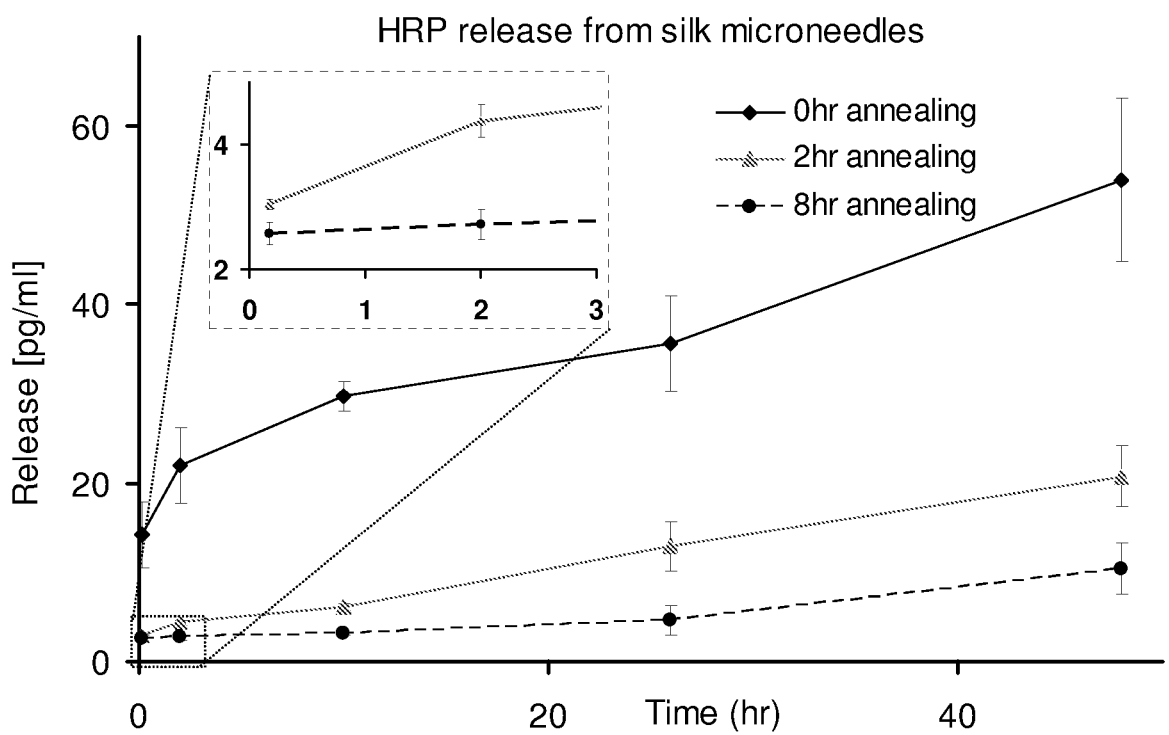

FIG. 9B depicts enzymatic activity of the HRP, which retained activity during silk processing and collagenase digestion and was detected by using a chromogenic substrate that turns blue in the presence of active HRP. The release kinetics of HRP from silk fibroin microneedles into the collagen hydrogels (N=3) were determined spectroscopically. The collagen hydrogel was selectively digested with collagenase. Subsequently, a colorimetric HRP enzyme activity assay was carried out as described later in the Exemplary Materials and Methods (FIG. 9C). The insert in FIG. 8C shows the initial HRP release in collagen hydrogels. A sustained release of HRP was observed over the entire test period (FIG. 9C). The maximum release of 54 pg of HRP per needle after 48 hours was observed in the untreated microneedles devices. Compared to the 2 hour and 8 hour water annealed devices, the untreated silk microneedles released in the same time period about 2.7±0.18 and about 5.6±0.99 times as much HRP, respectively. The beta sheet content in the silk fiborin microneedle samples was determined, e.g., by infrared spectroscopy [31], with results of ~14%, ~18% and ~21% for the untreated, 2 hr-annealed and 8 hr-annealed silk fibroin microneedle samples, respectively. Such findings indicate that the increased water vapor annealing time increased beta sheet content and reduced HRP release. Accordingly, by way of example only, water vapor annealing can be an exemplary method to treat silk fibroin microneedles for controlling the release of an active agent embedded inside the silk fibroin microneedles. In some embodiments, other post-processing methods can be used to modulate amount of beta sheet within silk fibroin to control drug release rate.

Furthermore, in some circumstances, administration of antibiotics can be desirable to prevent infection at sites of microneedle penetration. See, e.g., Donnelly et al. (2009) Pharm Res. 26: 2513-2522. To evaluate the efficacy of using silk fibroin microneedles to reduce infections, antibiotic-loaded silk fibroin microneedles were prepared and assessed. Tetracycline-loaded and plain silk fibroin microneedles (used as controls) were prepared as described herein. The silk fibroin microneedles arrays were used as described in FIG. 9A (i.e. only the microneedles are exposed) and affixed to the bottom of a cell culture plate using PDMS. Tryptic Soy Agar was added to each plate containing either loaded or unloaded microneedles arrays and allowed to gel. Subsequently, *Staphylococcus aureus* (*S. aureus*) bacteria were applied to each plate and incubated overnight at 37° C. to allow the formation of a bacterial lawn.

Figure 10A:
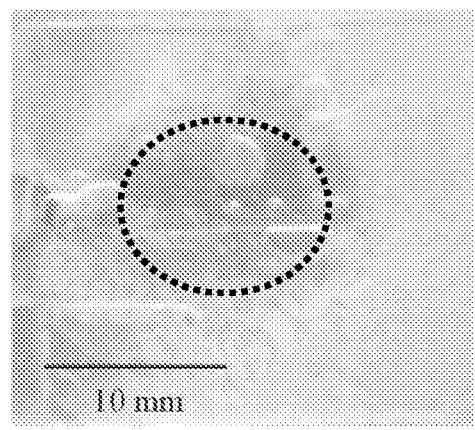
FIGS. 10A-10B show results of exemplary silk fibroin microneedles loaded with or without tetracycline antibiotics for use in controlling bacterial growth.
Figure 10A:
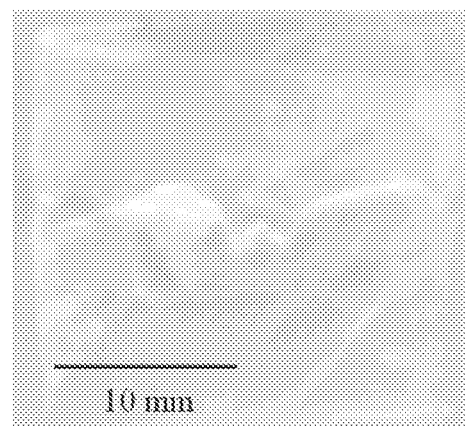
Figure 10B:
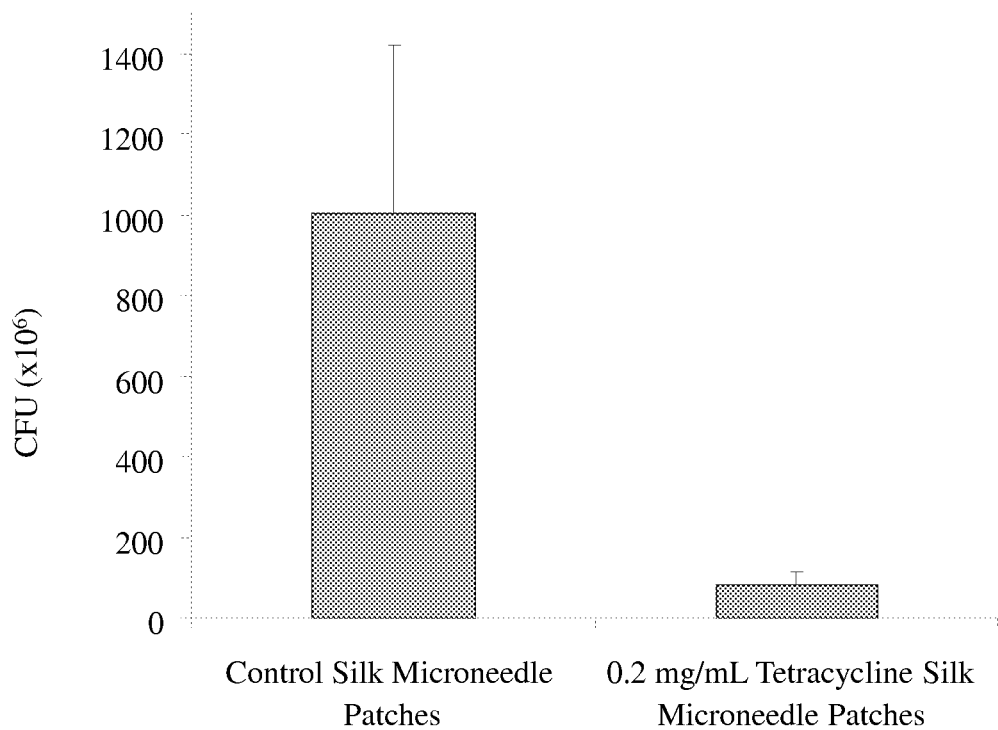

Tetracycline-releasing microneedles resulted in a visible decrease in bacterial density in the region of drug release (FIG. 10A). To quantify the bacterial density, a 10-mm diameter region of agar above the microneedle arrays was excised, homogenized in culture broth and plated in triplicate. The plated liquid cultures were incubated overnight at 37° C. to allow colony growth. A 10-fold decrease in colony forming units (in million CFU per excised area) for agar samples exposed to drug loaded silk fibroin microneedles was determined relative to the controls (FIG. 10B). The antibiotic-loaded microneedles inhibited the growth of bacteria.

Presented herein are one or more embodiments of fabricating high aspect ratio silk fibroin microneedles. The mild processing conditions during silk fibroin microneedle fabrication and the properties of the silk fibroin biomaterial can allow sensitive active agents (e.g., drugs such as antibiotics, as well as labile enzymes) to be incorporated and stored in the microneedles. For example, presented herein indicates that fabrication and post-treatment of silk fibroin microneedles all under mild ambient conditions can preserve function and control release of a large molecule from the microneedles. Furthermore, silk fibroin microneedles can be loaded with antibiotics to inhibit the growth of pathogens, which can offer an attractive strategy to prevent local infections. The silk fibroin-based microneedle systems presented herein recapitulate form and function, successfully addressing current limitations associated with other polymeric or metallic microneedle systems and providing an effective path for storage and delivery of drugs and therapeutics.

The silk fibroin microneedles or microneedle devices described herein can be used to meet a range of clinical needs, including sustained delivery of peptide therapeutics and vaccines with short half-lives [22]. In some embodiments, human growth hormone therapy [23, 38] and vaccines requiring long-term exposure [24] can benefit from some embodiments of the microneedles or microneedle devices described herein. The stabilizing effect of silk fibroin on incorporated active agents, such as proteins, can be combined with the convenience and self-administration of microneedles to produce drug delivery platforms that are safe and easy to self-administer and can be stored at elevated temperatures.

Exemplary Materials and Methods

Master Mold Fabrication:

The aluminum (Al) master was fabricated by computer numerical control CNC machining with a 0.5 mm, 15 deg end mill, in a custom made 70K rpm tool. The Al template was further processed by a timed (1.5 hours) chemical wet etch in Al etchant at 50° C. (Al etchant type A, 80% phosphoric acid, 5%, nitric acid, 5% acetic acid, and 10% distilled water).

Silk Extraction:

The process to obtain aqueous silk fibroin solution from *Bombyx mori* cocoons has been previously described in the art, e.g., [37]. Briefly, sericin was removed by boiling the cocoons in an aqueous sodium carbonate solution for about 40 minutes. After drying, the silk fibroin fibers were dissolved in lithium bromide solution and subsequently the salt was removed by dialysis against deionized (DI) water until the solution reached a concentration of about 6-8% wt/v.

HRP Release Model:

The silk fibroin microneedles were loaded with 1 mg/ml of HRP (Sigma Aldrich). The silk fibroin microneedle patches were treated by water vapor annealing for about 2 hours and about 8 hours to modify the release characteristics. Gelatin or collagen hydrogel was prepared by boiling 40 ml DI water and mixing it with 4.5 g of KNOX™ original unflavored gelatin powder to obtain a hydrogel at a concentration of about 0.112 g/ml. The solution was poured into a 100 mm diameter Petri dish and allowed to cool. The collagen or gelatin slab measured approximately 2.5 mm in height. The slabs were cut into 10 mm×5 mm sections. The silk microneedle patches were diced into 2 needles arrays. The needles were pierced through Parafilm (Parafilm M, Pechiney Plastic Packaging) membranes (polymer membrane in FIG. 8A) and subsequently applied to the hydrogel slabs to quantify the HRP release. All constructs were kept in a humid environment to avoid dehydration of the hydrogels. To quantify the total amount of HRP release from the silk fibroin microneedles, a plurality of stacks, each of which included an array of silk fibroin microneedles, a polymer membrane and a collagen hydrogel, were prepared and evaluated at multiple time points. At each indicated time point, the microneedles were removed from the hydrogel slab to stop further release of HRP. The hydrogel slabs were then digested in 400 µl of 1 mg/ml collagenase (Sigma Aldrich) for about 2 h at 36° C. Subsequently, HRP content was quantified according to an art-recognized protocol using TMB Peroxidase substrate (Bethyl Laboratories Inc). Briefly, the two substrate components (0.4 g/L solution of 3,3',5,5'-tetramthylbenzidine (TMB) and a 0.02% solution of $H_2O_2$ in citric acid) were brought to room temperature, mixed in equal volumes and added to samples containing HRP (including standards and experimental samples). Samples were incubated at room temperature approximately 5-10 minutes until sufficient color change was observed. An equal volume of $H_2SO_4$ was then added to stop color development. Absorbance was read with a microplate reader at a wavelength of 450 nm. Concentration standards with known amount of HRP were prepared under the same conditions in parallel.

Fourier Transform Infrared Spectroscopy (FTIR):

FTIR measurements (FT/IR-6200 Spectrometer, Jasco) and analysis was performed using any methods known in the art, e.g., the methods described in [31]. Fourier self-deconvolution of the infrared spectra of the amide I region was performed by OPUS 5.0 software (Bruker Optics). The deconvolution was performed with a half-bandwidth of 27 $cm^{-1}$ and a noise reduction factor of 0.3.

Antibiotic Loaded Silk Fibroin Microneedles and Bacterial Growth:

Silk fibroin microneedle patches loaded with 2 mg/ml tetracycline were fabricated as described herein. Tryptic Soy Agar was prepared according to manufacturer's instructions and aliquoted into 100 mm diameter Petri dish (15-20 mL per plate). Lyophilized S. aureus ATCC 25923 (American Type Culture Collection) bacteria cultures were reconstituted and expanded according to manufacturer instructions. To test susceptibility of bacteria exposed to antibiotic-loaded silk fibroin microneedles, liquid cultures were grown for 18-24 hours to an optical density ($OD_{600}$) between 1 and 1.2 (corresponding to a viable count of approximately $10^6$ CFU/mL). A 10-mm diameter biopsy (total area=approximately 78.5 $mm^2$) of agar was excised from above the microneedle arrays. The array samples were immersed in 10 mL of Tryptic Soy Broth and homogenized for 5-10 seconds. The homogenate was diluted and plated on Tryptic Soy Agar plates (0.5 mL of liquid culture per plate). After liquid cultures were incubated, the lowest dilution for which individual colonies were distinguishable was selected and colonies were counted (3 plates per sample, 3 samples per treatment type).

Other embodiments are within the scope and spirit of the invention. Further, while the description above refers to the invention, the description may include more than one invention.

REFERENCES

[1] A. Arora, M. Prausnitz, S. Mitragotri, International journal of pharmaceutics 2008, 364, 227.
[2] J. H. Park, M. G. Allen, M. R. Prausnitz, Pharmaceutical research 2006, 23, 1008.
[3] S. Sullivan, D. Koutsonanos, M. del Pilar Martin, J. Lee, V. Zarnitsyn, S. Choi, N. Murthy, R. Compans, I. Skountzou, M. Prausnitz, Nature medicine 2010, 16, 915.
[4] Y. C. Kim, F. S. Quan, R. W. Compans, S. M. Kang, M. R. Prausnitz, Journal of Controlled Release 2010, 142, 187.
[5] Y. C. Kim, F. S. Quan, R. W. Compans, S. M. Kang, M. R. Prausnitz, Pharmaceutical research 2011, 28, 135.
[6] R. F. Donnelly, D. I. J. Morrow, T. R. R. Singh, K. Migalska, P. A. McCarron, C. O'Mahony, A. D. Woolfson, Drug development and industrial pharmacy 2009, 35, 1242.
[7] S. Sullivan, N. Murthy, M. Prausnitz, Advanced Materials 2008, 20, 933.
[8] P. J. You X, Chang J., in IEEE International Conference on Nano/Molecular Medicine and Engineering: [proceedings], Institute of Electrical and Electronic Engineers; Piscataway, N.J., Red Hook, N.Y. 2010.
[9] S. Davis, B. Landis, Z. Adams, M. Allen, M. Prausnitz, Journal of biomechanics 2004, 37, 1155.
[10] C. Jiang, X. Wang, R. Gunawidjaja, Y. Lin, M. Gupta, D. Kaplan, R. Naik, V. Tsukruk, Advanced functional materials 2007, 17, 2229.
[11] G. Altman, F. Diaz, C. Jakuba, T. Calabro, R. Horan, J. Chen, H. Lu, J. Richmond, D. Kaplan, Biomaterials 2003, 24, 401.
[12] S. Lu, X. Wang, Q. Lu, X. Hu, N. Uppal, F. Omenetto, D. Kaplan, Biomacromolecules 2009, 217.
[13] S. Lu, X. Wang, Q. Lu, X. Hu, N. Uppal, F. Omenetto, D. Kaplan, Biomacromolecules 2009, 10, 1032.
[14] J. Amsden, H. Perry, S. Boriskina, A. Gopinath, D. Kaplan, L. Dal Negro, F. Omenetto, Optics Express 2009, 17, 21271.
[15] F. Omenetto, D. Kaplan, Nature Photonics 2008, 2, 641.
[16] H. Perry, A. Gopinath, D. Kaplan, L. Dal Negro, F. Omenetto, Advanced Materials 2008, 20, 3070.
[17] K. Tsioris, H. Tao, M. Liu, J. Hopwood, D. Kaplan, R. Averitt, F. Omenetto, Advanced Materials 2011, 23, 2015.
[18] J. Chen, N. Minoura, A. Tanioka, Polymer 1994, 35, 2853.
[19] X. Y. Liu, C. C. Zhang, W. L. Xu, C. Ouyang, Materials Letters 2009, 63, 263.
[20] S. Putthanarat, R. Eby, R. Naik, S. Juhl, M. Walker, E. Peterman, S. Ristich, J. Magoshi, T. Tanaka, M. Stone, Polymer 2004, 45, 8451.
[21] L. Uebersax, H. Hagenmuller, S. Hofmann, E. Gruenblatt, R. Muller, G. Vunjaknovakovic, D. L. Kaplan, H. P. Merkle, L. Meinel, Tissue Eng 2006, 12, 3417.
[22] C. Cullander, R. H. Guy, Advanced drug delivery reviews 1992, 8, 291.
[23] H. Kwak, W. Shim, M. Choi, M. Son, Y. Kim, H. Yang, T. Kim, G. Lee, B. Kim, S. Kang, Journal of Controlled Release 2009, 137, 160.
[24] J. Kemp, M. Kajihara, S, Nagahara, A. Sano, M. Brandon, S. Lofthouse, Vaccine 2002, 20, 1089.

[25] D. B. Wolfe, D. Qin, G. M. Whitesides, Methods Mol Biol 2010, 583, 81.
[26] S. Bhattacharya, A. Datta, J. M. Berg, S. Gangopadhyay, Microelectromechanical Systems, Journal of 2005, 14, 590.
[27] L. Fritz, D. Hofmann, Polymer 1997, 38, 1035.
[28] H. Jin, J. Park, V. Karageorgiou, U. Kim, R. Valluzzi, P. Cebe, D. Kaplan, Advanced Functional Materials 2005, 15, 1241.
[29] Q. Lu, X. Hu, X. Wang, J. A. Kluge, S. Lu, P. Cebe, D. L. Kaplan, Acta Biomaterialia 2010, 6, 1380.
[30] S. Hofmann, C. Wong Po Foo, F. Rossetti, M. Textor, G. Vunjak-Novakovic, D. Kaplan, H. Merkle, L. Meinel, Journal of controlled release 2006, 111, 219.
[31] X. Hu, D. Kaplan, P. Cebe, Macromolecules 2006, 39, 6161.
[32] E. M. Pritchard, C. Szybala, D. Boison, D. L. Kaplan, J Control Release 2010, 144, 159.
[33] X. Wang, X. Hu, A. Daley, O. Rabotyagova, P. Cebe, D. L. Kaplan, J Control Release 2007, 121, 190.
[34] G. Wightman, J. Beard, R. Allison, Forensic science international 2010, 200, 41.
[35] B. Forslind, M. Lindberg, G. M. Roomans, J. Pallon, Y. Werner-Linde, Microsc Res Tech 1997, 38, 373.
[36] W. Montagna, P. F. Parakkal, The structure and function of skin, Academic Press, New York, 1974.
[37] S. Sofia, M. B. McCarthy, G. Gronowicz, D. L. Kaplan, Journal of Biomedical Materials Research 2001, 54, 139.
[38] Lee et al., Dissolving microneedle patch for transdermal delivery of human growth hormone, Small 2011, 7: 531-539.

Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A microneedle device, comprising:
   a substrate and
   one or more silk fibroin microneedles comprising regenerated silk fibroin,
   wherein the one or more silk fibroin microneedles are integrated or attached to the substrate and extending from the substrate,
   wherein each silk fibroin microneedle comprises a base and a penetrating tip, and
   wherein the one or more silk fibroin microneedles degrade over a period of at least about 5 days upon contact with a biological barrier.

2. The microneedle device of claim 1, wherein the one or more silk fibroin microneedles further comprises at least one active agent.

3. The microneedle device of claim 1, wherein the one or more silk fibroin microneedles ranges from about 15 μm to about 1500 μm in length.

4. The microneedle device of claim 1, wherein the substrate comprises one or more biocompatible polymers.

5. The microneedle device of claim 1, wherein the substrate is flexible and conforms to a surface upon contact with the surface.

6. The microneedle device of claim 1, wherein the substrate comprises silk fibroin and is integrated with the one or more silk fibroin microneedles.

7. The microneedle device of claim 1, further comprising an adhesive.

8. The microneedle device of claim 1, wherein each silk fibroin microneedle has a tip dimension ranging from about 50 nm to about 50 pm.

9. The microneedle device of claim 1, wherein the regenerated silk fibroin is or comprises one or more of *Bombyx mori* silk fibroin, *Nephila clavipes* silk fibroin, transgenic silk fibroin and genetically engineered silk fibroin.

10. The microneedle device of claim 2, wherein the one or more silk fibroin microneedles delivers the active agent across or into a biological barrier.

11. The microneedle device of claim 10, wherein the biological barrier is a tissue of a subject chosen from a skin tissue, a mucosal tissue, a vascular tissue, a lymphatic vessel, an ocular tissues, or a cell membrane.

12. A microneedle device, comprising:
   a substrate and
   one or more silk fibroin microneedles comprising a transgenic silk or a genetically engineered silk, wherein the one or more silk fibroin microneedles are integrated or attached to the substrate and extending from the substrate,
   wherein each silk fibroin microneedle comprises a base and a penetrating tip, and
   wherein the one or more silk fibroin microneedles degrade over a period of at least about 5 days upon contact with a biological barrier.

13. The microneedle device of claim 12, wherein the genetically engineered silk is a silk from a bacterium, a yeast, a mammalian cell, a transgenic animal, or a transgenic plant.

14. The microneedle device of claim 1, wherein each silk fibroin microneedle has a tip dimension ranging from about 50 nm to about 10 μm, about 50 nm to about 8 μm, about 100 nm to about 5 μm, or about 100 nm to about 2 μm.

15. The microneedle device of claim 1, wherein each silk fibroin microneedle has a tip dimension ranging from about 100 nm to about 5 μm.

16. The microneedle device of claim 12, wherein each silk fibroin microneedle has a tip dimension ranging from about 100 nm to about 5 μm.

17. The microneedle device of claim 2, wherein the at least one active agent is selected from the group consisting of proteins, peptides, antigens, immunogens, vaccines, antibodies or portions thereof, enzymes, nucleic acids, siRNA, shRNA, aptamers, viruses, bacteria, small molecules, cells, hormones, antibiotics, therapeutic agents, diagnostic agents, and any combinations thereof.

18. The microneedle device of claim 1, wherein each silk fibroin microneedle has a tip dimension ranging from about 100 nm to about 5 μm, and is configured to penetrates the skin.

19. The microneedle device of claim 18, further comprising an active agent and delivering the active agent across or into the skin.

20. The microneedle device of claim 1, wherein the one or more silk fibroin microneedles degrade over a period of at least about 1 week upon contact with the biological barrier.

21. The microneedle device of claim 1, wherein the one or more silk fibroin microneedles degrade over a period of at least about 2 weeks upon contact with the biological barrier.

22. The microneedle device of claim 2, wherein the degradation of the one or more silk fibroin microneedles controls release of the at least one active agent.

23. The microneedle device of claim 12, wherein the one or more silk fibroin microneedles degrade over a period of at least about 1 week upon contact with the biological barrier.

24. The microneedle device of claim 12, wherein the one or more silk fibroin microneedles degrade over a period of at least about 2 weeks upon contact with the biological barrier.

* * * * *

UNITED STATES PATENT AND TRADEMARK OFFICE
CERTIFICATE OF CORRECTION

| | | |
|---|---|---|
| PATENT NO. | : 10,933,173 B2 | Page 1 of 1 |
| APPLICATION NO. | : 13/880592 | |
| DATED | : March 2, 2021 | |
| INVENTOR(S) | : David L. Kaplan et al. | |

It is certified that error appears in the above-identified patent and that said Letters Patent is hereby corrected as shown below:

In the Specification

Column 14, Lines 5-6, "normucleotide" should be --nonnucleotide--.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*